(12) United States Patent
Zhang et al.

(10) Patent No.: US 7,736,911 B2
(45) Date of Patent: Jun. 15, 2010

(54) ACTIVITY-BASED PROBES FOR PROTEIN TYROSINE PHOSPHATASES

(75) Inventors: Zhong-Yin Zhang, Scarsdale, NY (US); Sanjai Kumar, Middleton, CT (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 11/107,545

(22) Filed: Apr. 15, 2005

(65) Prior Publication Data

US 2005/0233469 A1 Oct. 20, 2005

Related U.S. Application Data

(60) Provisional application No. 60/562,574, filed on Apr. 15, 2004.

(51) Int. Cl.
G01N 33/533 (2006.01)
G01N 33/534 (2006.01)
G01N 21/76 (2006.01)
C12Q 1/42 (2006.01)
C07K 1/10 (2006.01)

(52) U.S. Cl. ............... 436/546; 436/545; 436/56; 436/172; 436/103; 436/124; 435/21; 530/402

(58) Field of Classification Search ................ 435/7.4, 435/21, 188, 968; 436/544, 545, 546, 103, 436/124, 815; 530/402, 403
See application file for complete search history.

(56) References Cited

U.S. PATENT DOCUMENTS 5,326,905 A 7/1994 Dow et al.
5,714,361 A 2/1998 Widlanski
5,763,577 A 6/1998 Bolton et al.

(Continued)

FOREIGN PATENT DOCUMENTS

WO WO 94/08600 4/1994

(Continued)

OTHER PUBLICATIONS

Zhu et al. Activity-based fluorescent probes that target phosphatases. Tetrahedron letters, 2003, vol. 44, pp. 2669-2672.*

(Continued)

*Primary Examiner*—Shafiqul Haq
(74) *Attorney, Agent, or Firm*—Amster, Rothstein & Ebenstein LLP

(57) ABSTRACT

Provided are compounds capable of covalently binding to a protein tyrosine phosphatase (PTP). The compounds comprise Formula A:

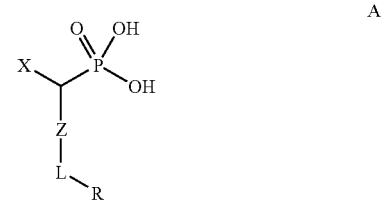

Also provided are compositions comprising one of the above compounds covalently bound to a member of the PTP superfamily, methods of labeling a PTP using the compounds, methods of isolating a PTP from a mixture of proteins using the compounds, methods of evaluating whether a substance is an inhibitor of a PTP using the compounds, methods of evaluating the specificity of an inhibitor of a PTP using the compounds, methods of identifying a PTP involved in a disease in a mammal using the compounds, and methods of diagnosing a disease in a mammal using the compounds.

17 Claims, 13 Drawing Sheets

BBP

I

II

U.S. PATENT DOCUMENTS

| | | | |
|---|---|---|---|
| 5,770,620 | A | 6/1998 | Mjalli et al. |
| 5,843,707 | A | 12/1998 | Larsen et al. |
| 5,919,813 | A | 7/1999 | De Juan, Jr. |
| 6,136,798 | A | 10/2000 | Cody et al. |
| 6,174,874 | B1 | 1/2001 | Wang et al. |
| 6,245,742 | B1 | 6/2001 | Battistini et al. |
| 6,284,914 | B1 | 9/2001 | Fujisawa et al. |
| 6,348,572 | B1 * | 2/2002 | Desmarais et al. .......... 530/331 |
| 6,365,592 | B1 | 4/2002 | Leblanc et al. |
| 6,448,429 | B1 | 9/2002 | Leblanc et al. |
| 6,465,444 | B2 | 10/2002 | Bayly et al. |
| 6,486,141 | B2 | 11/2002 | Lau et al. |
| 6,486,142 | B2 | 11/2002 | Leblanc et al. |
| 6,498,151 | B2 | 12/2002 | Li et al. |
| 6,583,126 | B2 | 6/2003 | Leblanc et al. |
| 6,586,467 | B2 | 7/2003 | Burgess et al. |
| 6,624,152 | B2 | 9/2003 | Adams et al. |
| 2002/0002149 | A1 | 1/2002 | Bayly et al. |
| 2002/0040003 | A1 | 4/2002 | Burgess et al. |
| 2002/0052344 | A1 | 5/2002 | Leblanc et al. |
| 2002/0052346 | A1 | 5/2002 | Lau et al. |
| 2002/0052347 | A1 | 5/2002 | Leblanc et al. |
| 2002/0058644 | A1 | 5/2002 | Leblanc et al. |
| 2002/0091104 | A1 | 7/2002 | Li et al. |
| 2003/0004162 | A1 | 1/2003 | Treadway |
| 2003/0083267 | A1 | 5/2003 | Adams et al. |
| 2003/0114703 | A1 | 6/2003 | Leblanc et al. |
| 2004/0002479 | A1 | 1/2004 | Wang et al. |
| 2004/0005632 | A1 * | 1/2004 | Erlanson et al. .............. 435/7.1 |
| 2004/0191926 | A1 * | 9/2004 | Zhang et al. ................. 436/518 |

FOREIGN PATENT DOCUMENTS

| | | |
|---|---|---|
| WO | WO 95/25118 | 9/1995 |
| WO | WO 97/40017 | 10/1997 |
| WO | WO 00/05246 | 2/2000 |
| WO | WO 03/035621 | 5/2003 |
| WO | WO 03/035621 A1 | 5/2003 |
| WO | WO 03/093498 A1 | 11/2003 |

OTHER PUBLICATIONS

Broadbridge et al. "p56$^{lck}$ SH2 Domain Binding Motifs From Bead Binding Screening of Peptide Libraries Containing Phosphotyrosine Surrogates" *Letters in Peptide Science* 6: 335-341 (1999).

Burke et al. "Nonhydrolyzable Phosphotyrosyl Mimetics for the Preparation of Phosphatase-Resistant SH2 Domain Inhibitors" *Biochemistry* 33: 6490-6494 (1994).

Burke, Jr. et al. "Preparation of Fluro- and Hydroxy-4-(phosphonomethyl)-D, L-phenylalanine Suitably Protected for Solid-Phase Synthesis of Peptides Containing Hydrolytically Stable Analogues of O-Phosphotyrosine" *J Ory Chem* 58: 1336-1340 (1993).

International Search Report and Written Opinion of the International Searching Authority for International Patent Application No. PCT/US2005/012661 mailed on Jan. 12, 2006.

Kole et al. "Phosphonate Inhibitors of Protein-Tyrosine and Serine/teronine Phosphatases" *Biochem Journal* 311: 1025-1031 (1995).

Kotoris et al. "Preparation of Chiral α-monofluoroalkylphosphonic Acids and Their Evaluation as Inhibitors of Protein Tyrosine Phosphatase 1B" *J Chem Soc Perkin Trans 1* pp. 1271-1281 (2000).

Kumar et al. "Activity-based Probes for Protein Tyrosine Phosphatases" *PNAS* 101(21): 7943-7948 (2004).

Taylor et al. "Quiescent Affinity Inactivators of Protein Tyrosine Phosphatases" *Bioorganic & Medicinal Chemistry* 4(9): 1515-1520 (1996).

Wang et al. "Naphthalenebis [α,α-Difluoromethylenephosphonates] as Potent Inhibitors of Protein Tyrosine Phosphatases" *Bioorganic & Medicinal Chemistry Letters* 8: 345-350 (1998).

Andersen et al. "Structural and Evolutionary Relationships Among Protein Tyrosine Phosphatase Domains" *Molecular and Cellular Biology* 21(21): 7117-7136 (2001).

Barford et al. "The Structure and Mechanism of Protein Phosphatases: Insight into Catalysis and Regulation" *Annu Rev Biophys Biomol Struct* 27: 133-164 (1998).

Bleasdale et al. "Small Molecule Peptidomimetics Containing a Novel Phosphotyrosine Bioisostere Inhibit Protein Tyrosine Phosphatase 1B and Augment Insulin Action" *Biochemistry* 40:5642-5654 (2001).

Burke et al. "Potent Inhibition of Insulin Receptor Dephosphorylation by a Hexamer Peptide Containing the Phosphotyrosyl Mimetic F2Pmp" *Biochemical and Biophysical Research Communications* 204(1): 129-134 (1994).

Charifson et al. "Peptide Ligands of pp60c-src SH2 Domains: A Thermodynamic and Structural Study" *Biochemistry* 36(21): 6283-6293 (1997).

Chen et al. "VHR and PTP1 Protein Phosphatases Exhibit Remarkably Different Active Site Specificities Toward Low Molecular Weight Nonpeptide Substrates" *Biochemistry* 35: 9349-9354 (1996).

Chen et al. "Why is Phosphonodifluoromehtyl Phenylalanine a More portent Inhibitory Moiety than Phosphonomethyl Phenylalanine Toward Protein-Tyrosine Phosphatases?" *Biochemical and Biophysical Research Communications* 216(3): 976-984 (1995).

Cohen et al. "The Development and Therapeutic Potential of Protein Kinases Inhibitors" *Current Opinion in Chemical Biology* 3: 459-465 (1999).

Cravatt et al. "Chemical Strategies for the Global Analysis of Protein Function" *Current Opinion in Chemical Biology* 4:663-668 (2000).

Desmarais et al. "[Difluro(phosphono)methyl]phenylalanine-containing Peptide Inhibitors of Protein Tyrosine Phosphatases" *Biochemical Journal* 337(2): 219-556 (1999).

Gajda "Preparation of Diethyl 1-Bromoalkylphosphonates" *Phosphorus, Sulfur, and Silicon* 53: 327-331 (1990).

Gavin et al. "Chiral Molecular Recognition in a Tripeptide Benzylviologen Cyclophane Host" *J Org Chem* 63: 7663-7669 (1998).

Gordon et al. "Applications of Combinatorial Technologies to Drug Discovery. 2. Combinatorial Organic Synthesis, Library Screening Strategies, and Future Directions" *Journal of Medicinal Chemistry* 37(10): 1385-1401 (1994).

Greenbaum "Epoxide Electrophiles as Activity-Dependent Cysteine Protease Profiling and Discovery Tools" *Chemistry & Biology* 7: 569-581 (2000).

Griffiths et al. "Intramolecular Cyclisation of 2-vinyl- and 2-allylbenzoylphosphonates with Trimethyl Phosphite via Carbene Intermediates" *ARKIVOC* 1(3): 304-311 (2000).

Huang et al. "Molecular Determinants of Substrate Recognition in Hematopoietic Protein-tyrosine Phosphatase" *J Biol Chem* 279: 52150-52159 (2004).

Huyer et al. "Affinity Selcetion from Peptide Libraries to Determine Substrate Specificity of Protein Tyrosine Phosphatases" *Analytical Biochemistry* 258(1): 19-30 (1998).

Iversen et al. "Structure-based Design of a Low Molecular Weight, Nonphosphorus, Nonpeptide and Highly Selective Inhibitor of Protein-tyrosine Phosphatase 1B" *The Journal of Biological Chemistry* 275(14): 10300-10307 (2000).

Jeffery et al. "Chemical Proteomics and its Application to Drug Discovery" *Current Opinion in Biotechnology* 14: 87-95 (2003).

Kumar et al. "Activity-Based Probes for Protein Tyrosine Phosphatases" *Proc Natl Acad Sci USA* 101(21): 7943-7948 (2004).

Lawrence et al. "Protein Kinase Inhibitors: The Tyrosine-Specific Protein Kinases" *Pharmacology & Therapeutics* 77(2): 81-114 (1998).

Lee et al. "Tripeptide Inhibitors of Yersinia Protein-tyrosine Phosphatase" *Bioorganic and Medicinal Chemistry Letters* 13: 2577-2581 (2003).

Li et al. "Form, Function, and Regulation of Protein Tyrosine Phosphatases and their Involvement in Human Diseases" *Seminars in Immunology* 12: 75-84 (2000).

Liu et al. "Activity-Based Protein Profiling: The Serine Hydrolases" *Proc Natl Acad Sci, USA* 96(26): 14694-14699 (1999).

Liu et al. "Acylsulfonamide-Containing PTP1B Inhibitors Designed to Mimic an Enxyme-bound Water of Hydration" *Bioorganic and Medicinal Chemistry Letters* 13: 3005-3007 (2003).

Lo et al. "Design and Synthesis of Class-Selective Activity Probes for Protein Tyrosine Phosphatases" *Journal of Proteome Research* 1: 35-40 (2002).

Mammen et al. "Polyvalent Interactions in Biological Systems: Implications for Design and Use of Multivalent Ligands and Inhibitors" *Angew Chem Int Ed* 37: 2754-2794 (1998).

McCain et al. "17 Tyrosine Phosphatases in Cancer: Targets for Therapeutic Intervention" *Topics in Current Genetics* 5: 359-374 (2004).

McCain et al. "Suramin Derivatives as Inhibitors and Activators of Protein-tyrosine Phosphatases" *The Journal of Biological Chemistry* 279(15): 14713-14725 (2004).

Montserat et al. "Potent Low Molecular Weight Substrates for Protein-tyrosine Phosphatase" *The Journal of Biological Chemistry* 271(13): 7868-7872 (1996).

Pacofsky et al. "Potent Dipeptide Inhibitors of the pp60x-src SH2 Domain" *Journal of Medicinal Chemistry* 41(11): 1894-1908 (1998).

Puius et al. "Identification of a Second Aryl Phosphate-binding Site in Protein-Tyrosine Phosphatase 1B: A Paradigm for Inhibitor Design" *PNAS* 94: 13420-13425 (1997).

Sarmiento et al. "Structural Basis of Plasticity in Protein Tyrosine Phosphatase 1B Substrate Recognition" *Biochemistry* 39(28): 8171-8179 (2000).

Sun et al. "Crystal Structure of PTP1B Complexed with a Potent and Selective Bidentate Inhibitor" *Journal of Biological Chemistry* 278(14): 12406-12414 (2003).

Sun et al. "Crystal Structure of the *Yersinia* Protein-tyrosine Phosphatase YopH Complexed with a Specific Small Molecule Inhibitor" *Journal of Biological Chemistry* 278(35): 33392-33399 (2003).

Taing et al. "Potent and Highly Selective Inhibitors of the Protein Tyrosine Phosphatase 1B" *Biochemistry* 38(12): 3793-3803 (1999).

Taylor et al. "Quiescent Affinity Inactivators of Protein Tyrosine Phosphatases" *Bioorganic & Medicinal Chemistry* 4(9): 1515-1520 (1996).

Vetter et al. "Assessment of Protein-tyrosine Phosphatases 1B Substrate Specificity Using Inverse Alanine Scanning" *The Journal of Biological Chemistry* 275(4): 2265-2268 (2000).

Vetter et al. "Combinatorial Chemistry and Petide Library Methods to Characterize Protein Phosphatases" *Methods in Enzymology* 366: 260-282 (2003).

Wrobel et al. "PTP1B Inhibition and Antihyperglycemic Activity in the ob/ob Mouse Model of Novel 11-Arylbenso[b]naphtha[2,3-d]thiophenes" *The Journal of Medicinal Chemistry* 42(17): 3199-3202 (1999).

Xie et al. "Cellular Effects of Small Molecule PTP1B Inhibitors on Insulin Signaling" *Biochemistry* 42: 12792-12804 (2003).

Zhang "Inhibitors of Protein Tyrosine Phosphatases" *Handbook of Cell Signaling* editors Bradshaw and Dennis, Elsevier Science, chapter 112, pp. 677-684 (2003).

Zhang et al. "Active Site Labeling of the *Yersinia* Protein Tyrosine Phosphatase: The Determination of the $pK_a$ of the Active Site Cysteine and the Function of the Conserved Histidine 402" *Biochemistry* 32: 9340-9345 (1993).

Zhang et al. "Chemical and Mechanistic Approaches to the Study of Protein Tyrosine Phosphatases" *Acc Chem Res* 36: 385-392 (2003).

Zhang et al. "Mechanistic Studies on Protein Tyrosine Phosphatases" *Progress in Nucleic Acid Research and Molecular Biology* 73: 171-220 (2003).

Zhang et al. "Protein Tyrosine Phosphatase Substrate Specificity: Size and Phosphotyrosine Positioning Requirements in Peptide Substrates" *Biochemistry* 33(8): 2285-2290 (1994).

Zhang et al. "Protein Tyrosine Phosphatases: Prospects for Therapeutics" *Current Opinion in Chemical Biology* 5(4): 416-423 (2001).

Zhang et al. "Protein-Tyrosine Phosphatases: Biological Function, Structural Characteristics and Mechanism of Catalysis" *Critical Reviews in Biochemistry and Molecular Biology* 33(1): 1-52 (1998).

Zhang et al. "PTP1B Inhibitors as Potential terapeutics in the Treatment of Type 2 Diabetes and Obesity" *Expert Opin Investig Drugs* 12(2): 223-233 (2003).

Zhang et al. "Substrate Specificity of the Protein Tyrosine Phosphatases" *PNAS* 90: 4446-4450 (1993).

Zhang et al. "The $Cyz(X)_5Arg$ Catalytic Motif in Phosphoester Hydrolysis" *Biochemistry* 33: 15266-15270 (1994).

Zhang et al. "The Single Sulfer to Oxygen Substitution in the Active Site Nucleophile of the Yersinia Protein-Tyrosine Phosphatase Leads to Substantial Structural and Functional Perturbations" *Biochemistry* 36(6); 1362-1369 (1997).

Zhang et al. "Thermodynamic Study of Ligand Binding to Protein-Tyrosine Phosphatase 1B and Its Substrate-Trapping Mutants" *Journal of Biological Chemistry* 275(44): 34205-34121 (2000).

Zhou et al. "Measuring Protein Phosphatases Activity with Physiological Substrates" *Methods in Enzymology* 366: 34-43 (2003).

Broadbridge & Sharma, "p56Ick SH2 domain binding motifs from bead binding screening of peptide libraries containing phosphotyrosine surrogates"; Letters in Peptide Science, 1999, vol. 6, pp. 335-341.

Burke, Jr. et al., "Preparation of Fluoro- and Hydroxy-4-(phosphonomethyl) -D,L-phenylalanine Suitably Protected for Solid-Phase Synthesis of Peptides Containing Hydrolytically Stable Analogues of O-Phosphotyrosine"; J. Org. Chem., 1993, vol. 58, No. 6, pp. 1336-1340.

Burke, Jr. et al., "Nonhydrolyzable Phosphotyrosyl Mimetics for the Preparation of Phosphatase-Resistant SH2 Domain Inhibitors"; Biochemistry, 1994, vol. 33, No. 21, pp. 6490-6494.

Kole H.K. et al., "Phosphonate inhibitors of protein-tyrosine and serine/threonine phosphatases"; Biochem. J., 1995, vol. 311, Part 3, pp. 1025-1031.

Kotoris C.C. et al., "Preparation of chiral alpha-monofluoroalkylphosphonic acids and their evaluation as inhibitors of protein tyrosine phosphatase 1B"; J. Chem. Soc., Perkin Trans., 2000, No. 7, pp. 1271-1281.

Wang Q. et al, "Naphthalenebis[alpha,alpha-Difluoromethylylenephosphonates] as potent inhibitors of protein tyrosine phosphatases"; Bioorganic & Medicinal Chemistry Letters, 1998, vol. 8, No. 4, pp. 345-350.

Gao, Y. et al., "Phosphotyrosyl-Based Motifs in the Structure-Based Design of Protein-Tyrosine Phosphatase Inhibitors"; American Chemical Society, Abstract of Paper 2000, vol. 219, p. MEDI27, XP-001002165, Abstract.

Burke, Jr. T.R. et al., "Small Molecule Interactions with Protein-Tyrosine Phosphatase PTP1B and Their Use in Inhibitor Design"; Biochemistry, 1996, vol. 35, pp. 15989-15996.

Yao Z.-J. et al., "Structure-based Design and Synthesis of Small Molecule Protein-Tyrosine Phosphtase 1B Inhibitors"; Bioorganic & Medicinal Chemistry, 1998, Vo. 6, pp. 1799-1810.

\* cited by examiner

BBP  I  II (a) Lissamine™ Rhodamine B–Probe (b) Cy5-Probe (a)

(b)

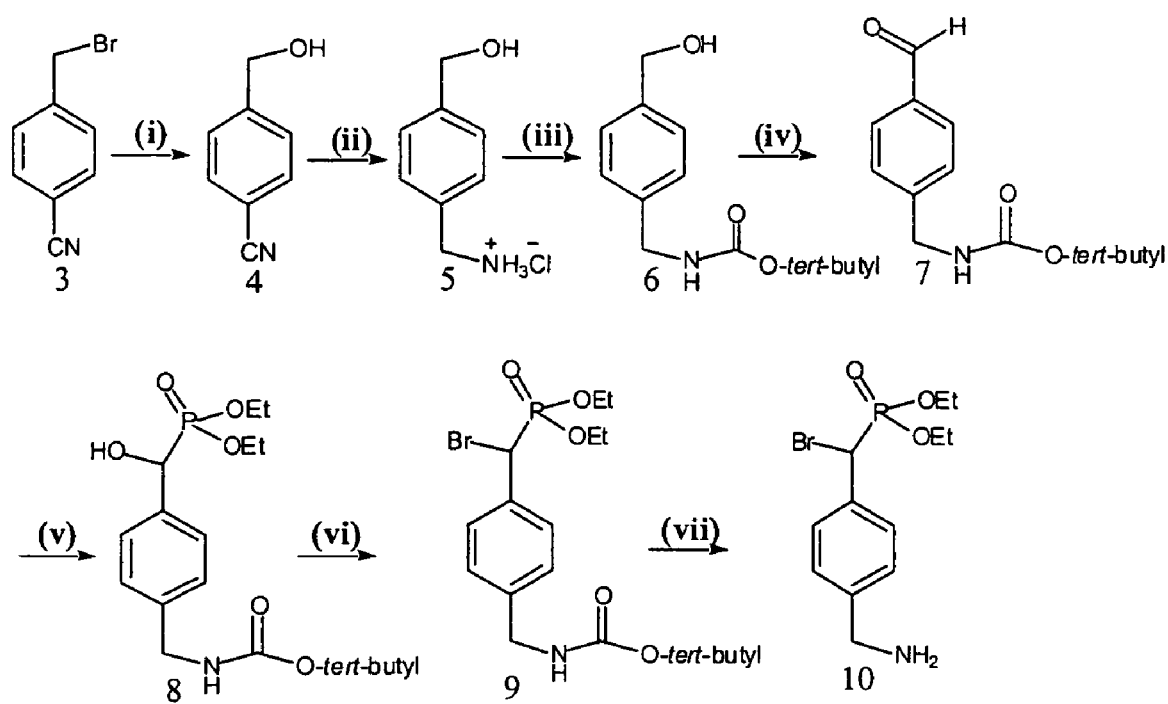
Scheme 1

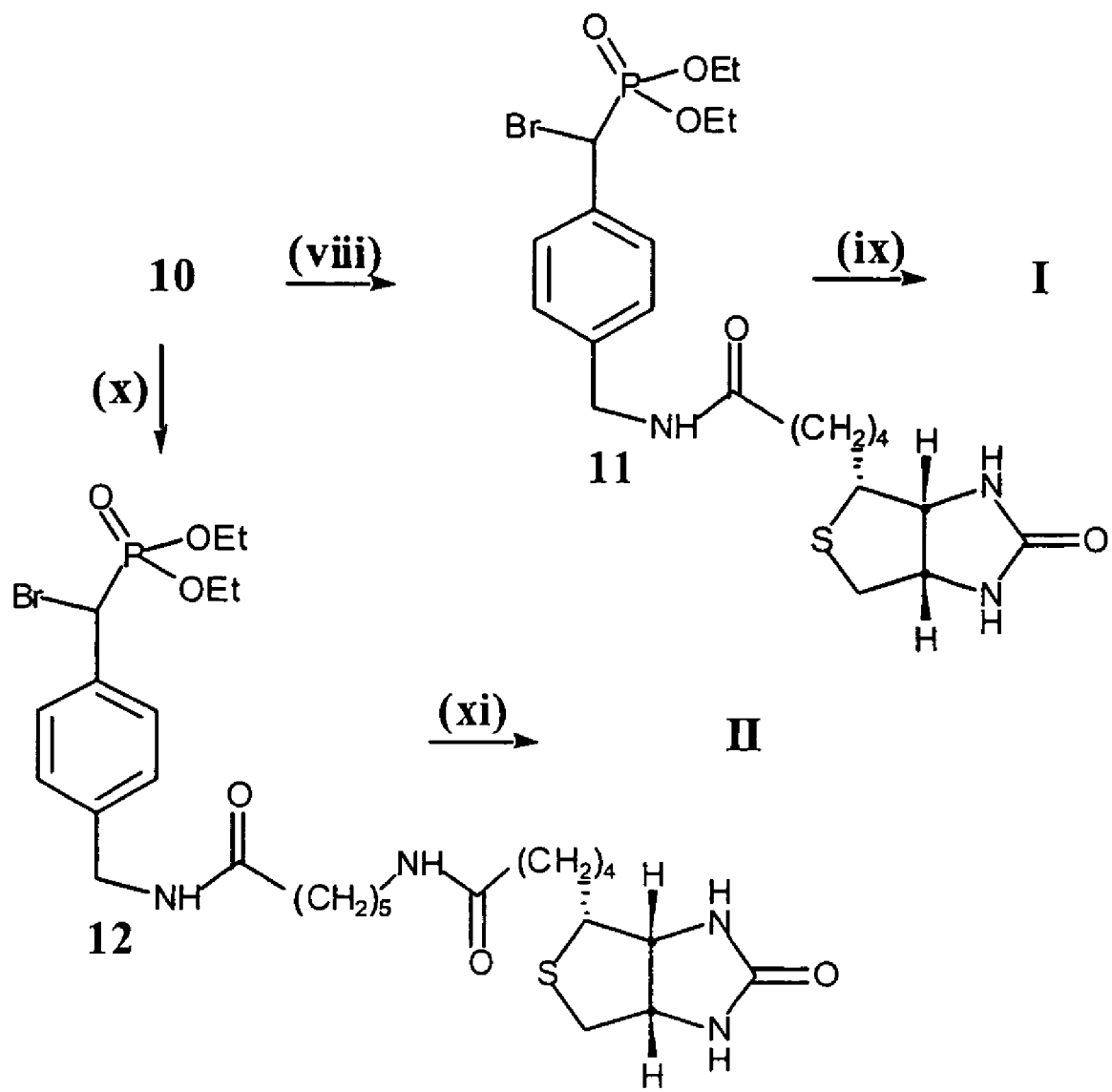
Scheme 2

ACTIVITY-BASED PROBES FOR PROTEIN TYROSINE PHOSPHATASES

RELATED APPLICATION INFORMATION

This application claims the benefit of U.S. Provisional Application No. 60/562,574, filed Apr. 15, 2004, which is incorporated by reference herein in its entirety.

STATEMENT OF GOVERNMENT SUPPORT

This invention was made with government support under Grant No. IU54 AI057158 awarded by the National Institutes of Health. The government has certain rights in the invention.

BACKGROUND (1) Field of the Invention

The present invention generally relates to compositions and methods of specifically labeling proteins. More particularly, the invention describes compositions that specifically bind to protein tyrosine phosphatases (PTPs), and methods for using those compositions for tracking PTP activity and for identifying and isolating PTPs.

(2) Description of the Related Art

REFERENCES CITED

Barford, D., Das, A. K., & Egloff, M. P. (1998) *Annu. Rev. Biophys. Biomol. Struct.* 27, 133-164.
Born, T. L., Myers, J. K., Widlanski, T. S., & Rusnak, F. (1995) *J. Biol. Chem.* 270, 25651-25655.
Corey, E. J. & Suggs, W. (1975) *Tetrahedron Lett.* 31, 2647-2650.
Cravatt, B. F. & Sorensen, E. J. (2000) *Curr. Opin. Chem. Biol.* 4, 663-668.
Far, A. R., Young, L. C., Rang, A., Rudkevich, D. M., & Rebek, J. Jr. (2002) *Tetrahedron* 58, 741-755.
Gavin, J. A., Garcia, M. E., Benesi, A. J., & Mallouk, T. E. (1998) *J. Org. Chem.* 63, 7663-7669.
Gajda, T. (1990) *Phosphorus Sulfur and Silicon* 53, 327-331.
Gavin, J. A., Garcia, M. E., Benesi, A. J., & Mallouk, T. E. (1998) *J. Org. Chem.* 63, 7663-7669.
Greenbaum, D., Medzihradszky, K. F., Burlingame, A., & Bogyo, M. (2000) *Chem. Biol.* 7, 569-581.
Hunter, T. (2000) *Cell* 100, 113-127.
Jeffery, D. A. & Bogyo, M. (2003) *Curr. Opin. Biotechnol.* 14, 87-95.
Kumar et al., (2004) *Proc. Natl. Acad. Sci. USA* 101:7943-7948
Li, L. & Dixon, J. E. (2000) *Semin. Immunol.* 12, 75-84.
Lo, L.-C., Pang, T.-L., Kuo, C.-H., Chiang, Y.-L., Wang, H.-Y. and Lin, J.-J. (2002) *J. Proteome Res.* 1, 35-40.
Liu, Y., Patricelli, M. P., & Cravatt, B. F. (1999) *Proc. Natl. Acad. Sci. USA* 96, 14694-14699.
McKenna, C. E., Higa, M. T., Cheung, N. H., & McKenna, M-C. (1977) *Tetrahedron Lett.* 2, 155-158.
Myers, J. K., & Widlansk, T. S. (1993) *Science* 262, 1451-1453.
Sun, J.-P., Wu, L., Fedorov, A. A., Almo, S. C. & Zhang, Z.-Y. (2003) *J. Biol. Chem.* 278, 33392-33399.
Taylor, W. P., Zhang, Z. Y., & Widlanski, T. S. (1996) *Bioorg. Med. Chem.* 4, 1515-1520.
Tonks, N. K. & Neel, B. G. (2001) *Curr. Opin. Cell Biol.* 13, 182-195.
Wang, Q., Dechert, U., Jirik, F., & Withers, S. G. (1994) *Biochem. Biophys. Res. Commun.* 200, 577-83.
Zhang, Z.-Y. (2001) *Curr. Opin. Chem. Biol.* 5, 416-423.
Zhang, Z.-Y. (2003) *Prog. Nucleic Acid Res. Mol. Biol.* 73,171-220.
Zhang, Z.-Y. & Dixon, J. E. (1993) *Biochemistry* 32, 9340-9345.
Zhang, Z.-Y., Wang, Y., Wu, L., Fauman, E., Stuckey, J. A., Schubert, H. L., Saper, M. A. & Dixon, J. E. (1994) *Biochemistry* 33, 15266-15270.
Zhang, Y.-L., Yao, Z.-J., Sarmiento, M., Wu, L., Burke, T. R. Jr. & Zhang, Z.-Y. (2000) *J. Biol. Chem.* 275, 34205-34212.

Protein tyrosine phosphatases (PTPs) constitute a large family of signaling enzymes (>100 in humans) that are important for the regulation of cell proliferation, differentiation, metabolism, migration, and survival (Hunter, 2000; Tonks & Neel, 2001). Dysfunction in PTPs results in aberrant tyrosine phosphorylation, which has been linked to the etiology of several human diseases, including cancer and diabetes (L1 & Dixon, 2000; Zhang 2001). Unlike protein kinases, where tyrosine specific and serine/threonine specific kinases share sequence identity, the PTPs show no sequence similarity with serine/threonine phosphatases, or the broad specificity phosphatases such as acid or alkaline phosphatases. The hallmark that defines the PTP superfamily is the active site amino acid sequence $C(X)_5R$, also called the PTP signature motif, in the catalytic domain. The PTPs can be broadly divided into two groups based on active site substrate specificity: the tyrosine-specific, and the dual specificity phosphatases, which hydrolyze pSer/Thr as well as pTyr. Despite variations in primary structure and differences in substrate specificity, key structural features in the active site and the mechanism of catalysis are conserved among all members of the PTP superfamily (Barford et al., 1998; Zhang, 2003).

Although PTPs share a common catalytic mechanism, they have distinct (and often unique) biological functions in vivo. One of the major challenges in the field is to rapidly establish the functional roles for PTPs, in both normal physiology and pathogenic conditions. Gene knockout analysis is useful to assess the role of a number of PTPs in cellular signaling. However, this process is often tedious, and gene ablation in animals often results in compensatory changes through other mechanisms during embryonic development. In addition, the one gene at a time approach is clearly inadequate to deal with the dynamics and complexity in the complement of proteins within a proteome. One attractive strategy for efficient analysis of PTP function is to characterize these enzymes collectively, rather than individually. In this regard, DNA microarray methods provide significant insights into changes in the abundance of transcripts. However, the measured mRNA levels do not always correlate with protein expression. Proteomic approaches address some of the gaps in genomic technologies by profiling and measuring bulk changes in protein levels. Unfortunately, current methodologies are only adequate for abundant proteins. Furthermore, the amount of protein is not always proportional to biological activity, which may subject to post-translational regulation. Thus, standard proteomics techniques are not optimal for tracking variations in protein activity. Because the function of a PTP depends on its phosphatase activity, the development of novel technologies for directly measuring the dynamics in PTP activity on a global scale is of tremendous interest.

Recently, a chemical approach has emerged that allows the consolidated detection and identification of collections of enzyme activities in complex proteomes (Cravatt & Sorensen, 2000; Jeffery & Bogvo, 2003). Such an approach employs specific chemical probes that are directed to enzyme active site for covalent modification in an activity dependent fashion. Activity-based probes have been used for proteomic analysis of the cysteine and serine hydrolases, providing new insights into our understanding of these two families of proteases in cell biology and in diseases (Liu et al., 1999; Greenbaum et al., 2000). However little success has been achieved in targeting specifically to the PTP family with activity-based probes.

Thus, there is a need for activity-based probes targeted to the PTP superfamily. The present invention satisfies that need.

SUMMARY OF THE INVENTION

Accordingly, the inventors have identified activity-based probes that covalently bind to all members of the protein tyrosine phosphatase (PTP) superfamily. These probes are useful for isolating and identifying PTPs in, e.g., tissues, cells, cellular extracts and/or biological fluids.

Thus, in some embodiments, the invention is directed to compounds capable of covalently binding to a protein tyrosine phosphatase (PTP). The compounds comprise Formula A:

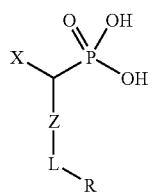

where Z is a monocyclic, heterocyclic, bicyclic or tricyclic moiety that is aromatic, where the L-R moiety and the phosphonate-containing moiety is covalently attached to Z at the meta or para positions, or are on different aromatic rings of Z; X is a good leaving group; R is a reporter moiety, an affinity moiety, or nothing, provided that when R is nothing, the compound comprises a radioactive moiety or an isotopic variant of any atom; and L is nothing or any moiety that does not cause steric hindrance preventing the compound from binding to the PTP, provided that L also prevents R from causing steric hindrance preventing the compound from binding to the PTP if R can otherwise cause such steric hindrance.

In other embodiments, the invention is directed to compositions comprising one of the above compounds covalently bound to a member of the PTP superfamily.

The invention is also directed to methods of labeling a PTP. The methods comprise combining the PTP with one of the above compounds, where R is a reporter moiety, under conditions and for a time sufficient for the PTP to covalently bind to the compound.

In additional embodiments, the invention is directed to methods of isolating a PTP from a mixture of proteins. The methods comprise combining the mixture with one of the above compounds, where R is an affinity moiety, under conditions and for a time sufficient for the compound to covalently bind to the PTP; then combining the mixture with a ligand of the affinity moiety; then washing the ligand to remove proteins that are not bound.

The invention is additionally directed to methods of evaluating whether a substance is an inhibitor of a PTP. The methods comprise combining the substance with the PTP and one of the above compounds, where R is a reporter moiety; and determining whether the compound is bound to the PTP. In these methods, a reduction in or lack of binding of the compound to the PTP indicates that the substance is an inhibitor of the PTP.

In further embodiments, the invention is also directed to methods of evaluating the specificity of an inhibitor of a PTP. The methods comprise combining the inhibitor with a mixture of PTPs with one of the above compounds, where R is a reporter moiety, and determining whether the compound is bound to each PTP in the mixture, where a reduction in or lack of binding of the compound to a PTP indicates that the inhibitor inhibits that PTP.

The invention is also directed to methods of identifying a PTP involved in a disease in a mammal. The methods comprise obtaining a first cellular extract from a mammal that has the disease and obtaining a second cellular extract from a mammal that does not have the disease; combining each cellular extract with one of the above compounds, where R is a reporter moiety; and assessing (e.g., quantifying) PTPs in each cellular extract by assessing (e.g., quantifying) the amount of reporter moiety bound to each PTP. In these embodiments, the presence of a greater amount of a PTP in one of the cellular extracts over the other cellular extract indicates that the PTP is involved in the disease.

In other embodiments, the invention is directed to methods of diagnosing a disease in a mammal, where the disease is characterized by the presence or change in expression of at least one PTP. The methods comprise obtaining a first cellular extract from a mammal that has the disease and obtaining a second cellular extract from a mammal that does not have the disease; combining each cellular extract with one of the above compounds, where R is a reporter moiety; and identifying any disease-associated PTP from the PTPs bound to the reporter moiety. In these embodiments, if the presence or quantity of any PTP associated with the disease is consistent with the presence of the disease, then the diagnosis is that the mammal has the disease.

Figure 1:
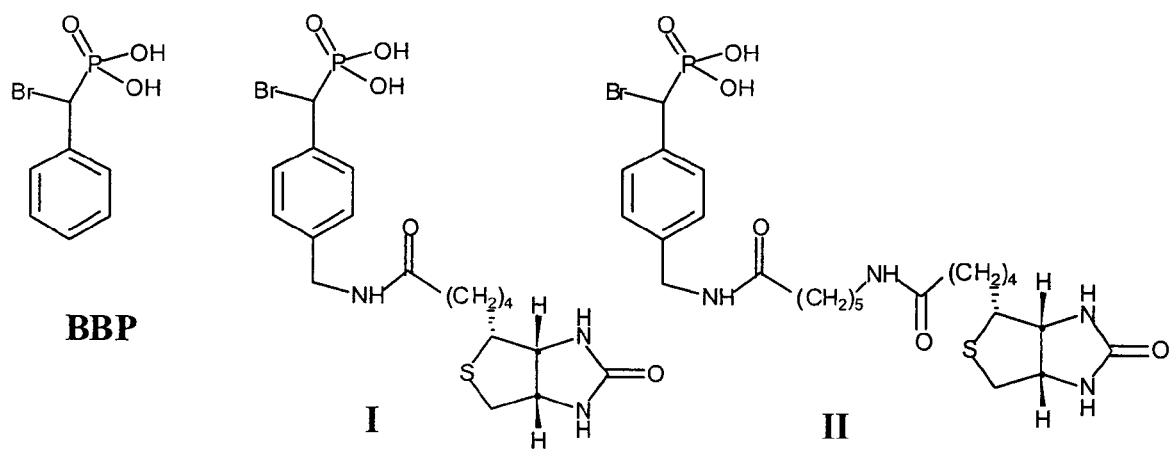
FIG. 1 shows the structures of α-bromobenzylphosphonate (BBP), and the PTP activity probes I and II.

Scheme 1 shows a synthetic route applied to the syntheses of common intermediate 10: (i) BaCO$_3$/H$_2$O, reflux, 2-2.5 h. (ii) LiAlH$_4$/ether, rt 45 min., Reflux 3 h. (iii) di-tert-butyl dicarbonate, KOH/THF/H$_2$O, rt 1.25 h, (iv) PCC/CH$_3$COONa, CH$_2$Cl$_2$, rt dark 17 h. (v) HPO(OEt)$_2$/Triethylamine, Benzene, reflux 50 hr. (vi) PPh$_3$Br$_2$, CH$_3$CN/Pyridine, 0° C. 1.5 hrs, rt 2 h. (vii) TFA neat, 15-20 min.

Scheme 2 shows the synthesis of compound I and II from common intermediate 10: (viii) (+) Biotinamido-N-hydroxysuccinimide ester/DMF, rt 70 h. (ix & xi) TMSBr/DMF, rt 18 h. (x) (+) Biotinamidohexanoic acid N-hydroxysuccinimide ester/DMF, rt 70 h.

DETAILED DESCRIPTION OF THE INVENTION

The present invention is based on the identification of activity-based probes that covalently bind to all members of the protein tyrosine phosphatase (PTP) superfamily (see Examples). These probes are useful for, e.g., isolating and identifying PTPs for research or diagnostic purposes.

Thus, in some embodiments, the invention is directed to compounds capable of covalently binding to a protein tyrosine phosphatase (PTP). The compounds comprise Formula A:

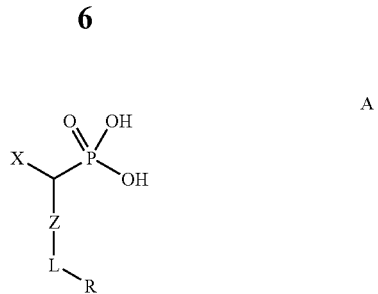

where Z is a monocyclic (e.g., benzene), heterocyclic (e.g., a purine), bicyclic (e.g., naphthalene) or tricyclic (e.g., anthracene) moiety that is aromatic, where the L-R moiety and the phosphate-containing moiety is covalently attached to Z at the meta or para positions, or are on different aromatic rings of Z; X is a good leaving group; R is a reporter moiety, an affinity moiety, or nothing, provided that when R is nothing, the compound comprises a radioactive moiety or an isotopic variant of any atom; and L is nothing or any moiety that does not cause steric hindrance preventing the compound from binding to the PTP, provided that L also prevents R from causing steric hindrance preventing the compound from binding to the PTP if R can otherwise cause such steric hindrance.

In preferred embodiments, X is a halide, an azide, a sulfonate, a tosylate, a carboxylate, an aryloxy carbonyl, an alkyloxy carbonyl, an aryl- or alkyl-carbonate, an imidazolide, a C1-C4 alkoxy, or a C1-C4 aryloxy. In more preferred embodiments, X is a halide, most preferably Br (see Examples).

In some embodiments, R is a reporter moiety, i.e., a detectable moiety, allowing detection of the PTPs bound to the compound. The reporter moiety can be directly detectable, or detectable after further treatment, e.g., with a labeled antibody that is specific for the reporter moiety. The scope of the invention is not limited to any particular reporter moiety for R. The skilled artisan can select and incorporate any appropriate reporter moiety at the R position without undue experimentation. Nonlimiting examples of useful reporter moieties that can be incorporated at the R position are: proteins such as green fluorescent protein, antibodies or antigen binding regions of antibodies (e.g., a FAb region), or enzymes for which there is a substrate that the enzyme converts into a detectable product, such as peroxidase or alkaline phosphatase; biotin; a fluorescent moiety, a chemiluminescent moiety; a colorimetric moiety; an antigen such as a hapten; a spin label; or a radioactive moiety. Preferably, R is a small compound such as biotin, to minimize interference with the compound-PTP binding. In other particular embodiments, R comprises a fluorescent probe including but not limited to Lissamine™ rhodamine B and Cy5.

In other embodiments, R is an affinity moiety, i.e., a moiety having a binding partner, to facilitate isolation of PTPs bound to the compound. Preferred examples include biotin, an oligo-His moiety, and an antigen, e.g., a hapten such as digoxigenin. It is noted that some reporter moieties are also affinity moieties, e.g., biotin and haptens.

The L moiety can be nothing or any moiety that does not cause steric hindrance preventing the compound from binding to the PTP. In cases where R would otherwise cause steric hindrance preventing the compound from binding to a PTP, L can be any moiety that prevents such steric hindrance.

In particular embodiments, the L moiety is any group sufficiently small to avoid steric hindrance to the compound's binding to the PTP. In general L will have a molecular weight less than about 200 or 500 daltons. The L moiety may, for example, be cyano, C1-C6 or C10 alkyl (which alkyl may be linear or branched, saturated or unsaturated, and substituted or unsubstituted), or C1-C5 or C6 aryl (which aryl may optionally contain 1, 2 or 3 hetero atoms selected from N, O, and S, and which aryl may be substituted or unsubstituted).

In preferred embodiments when R would otherwise cause such steric hindrance, L-R is —$CH_2$—NH—R or —$CH_2$—NH—C(O)—$(CH_2)_n$—NH—R, where n=1-10, preferably 5.

Any of the above-described compounds can also comprise an isotopic variant for any atom. As used herein, an "isotopic variant" is an isotope of a chemical element that is not the most abundant isotope of that element. Examples include deuterium, $^{15}N$, or $^{34}S$. The compounds of the invention, having an isotopic variant, are particularly useful for determining the mass of the PTP bound to the compound, or in determining partial peptide sequencing of the PTP, particularly near the active site of the PTP (where the compound is bound).

Figure 9:
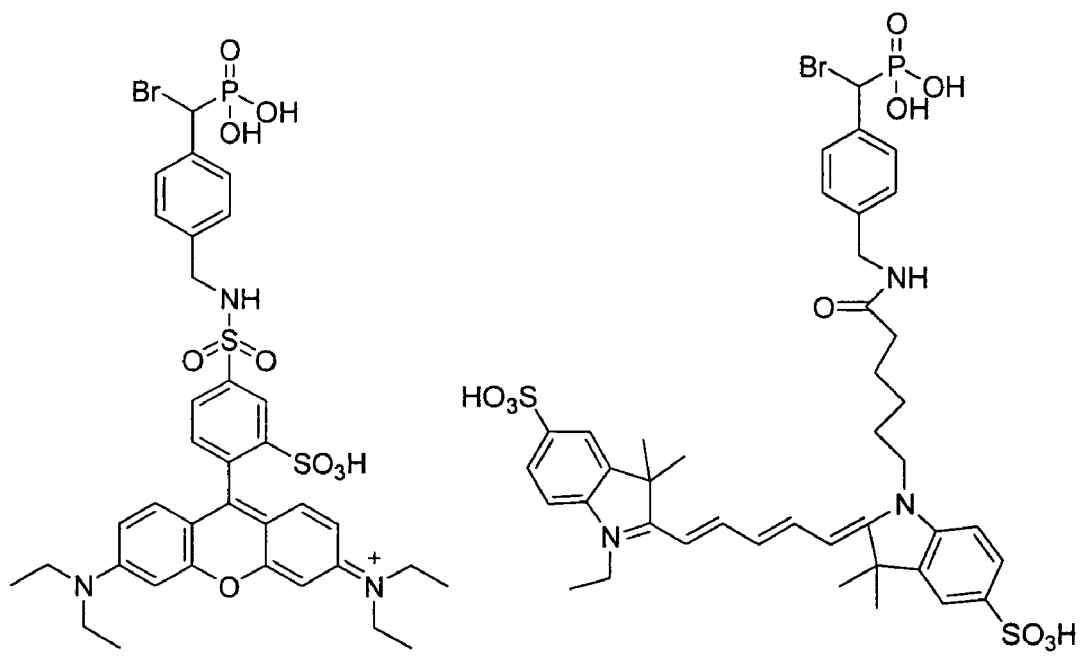
FIG. 9 shows the structure of: (a) a Lissamine™ rhodamine B-probe, and (b) a Cy5-probe.

In the most preferred embodiments, the compound consists of I or II of FIG. 1 or compound (a) or (b) of FIG. 9.

Any of the above-described compounds can be made using routine methods. See, e.g., the Examples for the application of various such methods, as well as establishing that the compounds bind to members of the PTP superfamily.

In other embodiments, the invention is directed to compositions comprising any of the above-described compounds, covalently bound to a member of the PTP superfamily. Such compositions can be produced by simply combining the compound with the PTP, e.g., under the conditions described in the Examples. Any member of the PTP superfamily, from any organism including any eukaryote, prokaryote or archaea, can be used in these compositions, including (but not limited to) any PTP1B, YopH, SHP1, SHP2, MEG2, PTPX1, PTPX10, PEST, LyPTP, MEG1, BDP1, PTPH1, PTPD1, PTPD2, PTPBAS, PTPTyp, CD45, PTPλ, LAR, HePTP, PTPaD45, PTPα, PTPβ, PTPε, PTPγ, PTPζ, or PTPIA2.

The invention is also directed to methods of labeling a PTP. The methods comprise combining the PTP with one or more of the above compounds, where R is a reporter moiety, under conditions and for a time sufficient for the PTP to covalently bind to the compound(s). These methods can be used to label a PTP either in a pure composition or in a mixture of compounds. It is envisioned that these methods are particularly useful for labeling PTPs in tissue, cells or cellular extracts, either from tissue culture or from an animal, e.g., a blood sample or a tissue biopsy, for any purpose, for example, in determining whether amounts of PTPs vary in particular tissues of an animal under various environmental or physiological conditions, or in animals of various genotypes; or in labeling more than one PTP present in a cellular extract of, e.g., a mammal such as a human, as part of a proteome analysis, or in determining whether a PTP expression profile (preferably, a quantitative PTP expression profile) varies under disease conditions. It is also envisioned that these labeling methods are useful in evaluating the role of PTPs in various cancers, diabetes (e.g., type I or type II), metabolic syndrome, inflammatory diseases, obesity, an infection by an organism that has a PTP, or an autoimmune disease, or in diagnosing any of those diseases. It is useful in several of these applications to assess (e.g., quantify) the active PTPs bound to the compound. Preferably, this is accomplished by assessing or quantifying the amount of reporter moiety bound to the PTP. Methods for assessing and/or quantifying any reporter moiety is within the skill of the art.

In additional embodiments, the invention is directed to methods of isolating a PTP from a mixture of proteins, preferably a cellular extract, e.g., from a mammal such as a human. These methods comprise combining the mixture with one or more of the above compounds, where R is an affinity moiety, under conditions and for a time sufficient for the compound to covalently bind to the PTP; then combining the mixture with a ligand of the affinity moiety; then washing the ligand to remove proteins that are not bound. These affinity-based isolation methods are known in the art, and preferably utilize a ligand that is part of the matrix of a chromatography column or a matrix in the form of a bead. In one preferred embodiment, the affinity moiety is a biotin and the ligand is a matrix comprising avidin.

In these embodiments, where the mixture of proteins (e.g., the cellular extract) comprises more than one PTP, the method would isolate all PTPs in the mixture, which is useful for, e.g., evaluating the profile of PTPs in the cells, etc.

Upon isolation of the PTP(s) from a mixture of proteins such as a cellular extract, the PTP or PTP(s) can be identified, e.g., with specific antibodies, by determination of molecular mass, by partial amino acid sequencing, and/or by evaluating the range of substrates of the PTP, using known methods. In many cases this involves separating the ligand from the affinity moiety, which can be done by routine methods. If there is more than one PTP in the mixture, they can also be further separated by known column or gel chromatography methods, e.g., 1D or 2D gel chromatography. If an isolated PTP is unknown, it can be further characterized by cloning, characterization of its substrates, physical characterization such as determining its mass (e.g., with mass spectroscopy) and/or charge characteristics, and/or its partial amino acid sequence, etc., all methods that are known in the art.

These methods are useful for evaluating the role of PTPs in disease (preferably mammalian disease, and most preferably human disease, or disease in a mammal that is a model for a human disease), or diagnosing a disease where a PTP is involved. When more than one PTP is involved, these methods are also useful for determining whether the profile of activity of the various PTPs is diagnostic of the disease. Examples of such diseases where PTPs are involved are various cancers, diabetes (e.g., type I or type II), metabolic syndrome, inflammatory diseases, obesity, an infection by an organism that has a PTP, and autoimmune diseases.

The present invention is also useful in identifying and characterizing inhibitors of a PTP, since the binding of an inhibitor to the PTP reduces or prevents binding of any the above-described compounds to the PTP. Binding of the inhibitor would therefore reduce or prevent labeling of the PTP with the compound comprising a reporter moiety. Thus, the invention is additionally directed to methods of evaluating whether a substance is an inhibitor of a PTP. The methods comprise combining the substance with the PTP and one or more of the above compounds, where R is a reporter moiety; and determining whether the compound is bound to the PTP. In these methods, a reduction in (e.g., by 25%, 35%, 50%, 65%, 75%, 85%, 90%, 95%, 98% or more) or lack of binding of the compound to the PTP indicates that the substance is an inhibitor of the PTP. In preferred embodiments of these methods, the compound not bound to the PTP is separated from the compound bound to the PTP, e.g., by chromatographic methods, then the bound compound is quantified, e.g., with a labeled antibody to the PTP, a labeled antibody to the reporter moiety, or a labeled non-antibody ligand of the reporter moiety; by measurement of radioactivity of the compound, measurement of a spin label on the compound, or by measurement of fluorescence of the compound.

In further embodiments, the invention is also directed to methods of evaluating the specificity of an inhibitor of a PTP. The methods comprise combining the inhibitor with a mixture of PTPs with one or more of the above compounds, where R is a reporter moiety, and determining whether the compound is bound to each PTP in the mixture, where a reduction in (e.g., by 25%, 35%, 50%, 65%, 75%, 85%, 90%, 95%, 98% or more) or lack of binding of the compound to a PTP indicates that the inhibitor inhibits that PTP. As with the previously described embodiments, the compound not bound to the PTP is preferably separated from the compound bound to the PTP, e.g., by chromatographic methods, then the bound compound is quantified, e.g., with a labeled antibody to the PTP, a labeled antibody to the reporter moiety, or a labeled non-antibody ligand of the reporter moiety; by measurement of radioactivity of the compound, measurement of a spin label on the compound, or by measurement of fluorescence of the compound.

The invention is also directed to methods of identifying a PTP involved in a disease in a mammal. The methods comprise obtaining a first cellular extract from a mammal that has the disease and obtaining a second cellular extract from a mammal that does not have the disease; combining each cellular extract with one or more of the above compounds, where R is a reporter moiety; and assessing or determining (e.g., quantifying) PTPs in each cellular extract by assessing or determining (e.g., quantifying) the amount of reporter moiety bound to each PTP. In these embodiments, the presence of a greater amount of a PTP in one of the cellular extracts over the other cellular extract indicates that the PTP is involved in the disease. The assessment or determination can be qualitative, semi-quantitative or quantitative in nature. Preferably, the disease is a cancer, diabetes (type I or type II), metabolic syndrome, an inflammatory disease, obesity, an infection by an organism that has a PTP, or an autoimmune disease. The PTP can also be further characterized, as described above.

In other embodiments, the invention is directed to methods of diagnosing a disease in a mammal, where the disease is characterized by the presence or change in expression of a PTP, or the presence or change in the expression profile of the PTP superfamily. The methods comprise obtaining a first cellular extract from a mammal that has the disease and obtaining a second cellular extract from a mammal that does not have the disease; combining each cellular extract with one or more of the above compounds, where R is a reporter moiety; and identifying any disease-associated PTP from the PTPs bound to the reporter moiety. In these embodiments, if the presence or quantity of any disease-associated PTP, or the expression profile of the PTPs identified, is consistent with the presence of the disease, then the diagnosis is that the mammal has the disease.

As discussed above, the present invention can be practiced to evaluate or assess the role of a PTP(s) in a disease and/or to diagnose a disease in a mammalian subject. Illustrative diseases include but are not limited to a cancer (tumor and/or non-tumor forming cancers), diabetes (type I or type II), metabolic syndrome, inflammatory disease, obesity, an infection by an organism that has a PTP, an autoimmune disease, cardiovascular disease, cystic fibrosis and other diseases of the lung, hemophilia A, hemophilia B, thalassemia, anemia and other blood disorders, AIDS, Alzheimer's disease, multiple sclerosis, Parkinson's disease, Huntington's disease, amyotrophic lateral sclerosis, epilepsy, and other neurological disorders, muscular dystrophies including Duchenne and Becker, Gaucher disease, Hurler's disease, adenosine deaminase deficiency, glycogen storage diseases, Pompe disease, and other metabolic defects, congenital emphysema, Lesch-Nyhan Syndrome, Niemann-Pick disease, Tays Sachs disease, Maple Syrup Urine Disease, retinal degenerative diseases, kidney deficiency, arthritis and organ rejection.

The methods of the invention can be practiced with any suitable biological sample, including tissue (e.g., a tissue biopsy or cultured tissue), cells, cellular extracts and biological fluids. Cells (and extracts derived therefrom) can be from primary cells, cultured cells or cell lines. Suitable biological samples include blood, plasma, lymph, cerebrospinal fluid and tissues, cells and extracts thereof derived from neural tissue (including the peripheral and central nervous systems, in particular, the brain), lung, the eye (including retina, retinal pigment epithelium, and cornea), epithelium (e.g., gut and respiratory epithelia), skeletal muscle, dendritic cells, pancreas (including islet cells), liver, heart, bone (e.g., bone marrow stem cells), hematopoietic stem cells, spleen, keratinocytes, fibroblasts, endothelium, prostate, and germ cells, as well as cancer or tumor tissue, cells and extracts thereof.

The methods of the invention can be practiced on and/or employ biological samples from any suitable mammalian subject, including but not limited to humans, non-human primates, dogs, cats, rats, mice, hamsters, rabbits, sheep, goats, horses, pigs, cattle, fish and the like.

Preferred embodiments of the invention are described in the following Examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the Examples.

Example 1

Bromobenzylphosphonate Probes for Protein Tyrosine Phosphatases

Example Summary

Protein tyrosine phosphatases (PTPs) are involved in the regulation of many aspects of cellular activity including proliferation, differentiation, metabolism, migration, and survival. Given the large number and complexity of PTPs in cell signaling, new strategies are needed for the integrated analysis of PTPs in the whole proteome. Unfortunately, the activities of many PTPs are tightly regulated by post-translational mechanisms, limiting the utility of standard genomics and proteomics methods for functional characterization of these enzymes. To facilitate the global analysis of PTPs, we designed and synthesized two activity-based probes that consist of α-bromobenzylphosphonate as a PTP specific trapping device, and a linker that connects the trapping device with a biotin tag for visualization and purification. We showed that these probes are active site-directed irreversible inactivators of PTPs, and form covalent adduct with PTPs involving the active site Cys residue. Additionally, we demonstrated that the probes are extremely specific toward PTPs while remaining inert to other proteins, including the whole proteome from *E. coli*. Consequently, these activity-based PTP probes can be used to profile PTP activity in complex proteomes. The ability to interrogate the entire PTP family on the basis of changes in their activity should greatly accelerate both the assignment of PTP function and the identification of potential therapeutic targets.

Introduction

Here, we describe the chemical synthesis and biochemical characterization of two activity-based probes that enable the interrogation of the state of PTP activity in samples of high complexity and in the whole proteome. It is anticipated that effective application of the activity-based PTP probes will accelerate the functional characterization of PTPs, thereby facilitating our understanding of the roles of PTPs in health and diseases.

Experimental Procedures

Organic synthesis of α-Bromobenzylphosphonate (BBP)-based Probes I and II. The reagents for the organic syntheses were purchased from Sigma-Aldrich Corp. All the moisture sensitive reactions were carried out strictly in an argon atmosphere. The fluorescent thin layer chromatography plates were purchased from Fisher Scientific. Flash chromatography was performed using Silica gel Merck grade 9385 (230-400 mesh, 60A). Purification of the final products was achieved by semi-preparative reverse phase HPLC on a C18 column. Characterizations of the molecules were done by NMR spectroscopy on a Bruker DRX-300 MHz spectrometer and ESI-MS (Shimadzu Corp.).

The chemical route applied to the syntheses of I and II are shown in Scheme 2.

4-Hydroxymethyl-benzyl-ammonium chloride (5): This was synthesized with a slight modification of the previously described protocol (Gavin et al., 1998). In a three neck flask under an argon atmosphere, was added an ice-cooled solution of 4 (2 g, 11.5 mmol) (prepared from commercially available material 3) in anhydrous diethyl ether (20 ml) (Gavin et al., 1998). To this was added in drops, lithium aluminum hydride solution (60 ml of 1M solution in anhydrous ether) over 45 minutes with constant stirring. The resulting mixture was then removed from ice bath and refluxed in oil bath for 3 h. The reaction was terminated by the slow addition of cold 0.1 M sodium hydroxide (150 ml) into the ice-cooled reaction flask. After removing the ether by rotary evaporation, the aqueous layer was extracted 4×100 ml chloroform. The combined organic layers were then back extracted into 3×100 ml 0.1 M hydrochloric acid. The aqueous layer was freeze-dried to yield 5 in 63% (1.63 g) yield. $^1$H NMR (300 MHz, DMSO) δ: 4.0 (t, J=1.8 Hz, 2H), 4.5 (s, 2H), 7.3-7.4 (m, 4H), 8.3 (br S, 2H).

(4-Formyl-benzyl)-carbamic acid tert-butyl ester (7): To a solution of crude 6 (3.11 g, 13.1 mmol) (Far et al., 2002) in methylene chloride (45 ml) was added the Corey regent (Corey & Suggs, 1975), and a mixture of pyridinium chlorochromate (2.26 g, 10.5 mmol) and sodium acetate (0.206 mg, 2.5 mmol). The mixture was stirred in dark at room temperature for about 17 h. The reaction mixture was triturated with ether (260 ml) and the catalyst, PCC, was filtered off upon passing through a celite bed. The organic filtrate was washed with water (260 ml) and the resulting aqueous layer was extracted with ether (260 ml). The combined organic layers were dried on anhydrous sodium sulfate and rotary evaporated to dryness. The purification on silica gel chromatography using 30% ethyl acetate and 5% triethylamine in hexane ($R_f$=0.45) gave 7 (1.56 g) as an oil in 50% yield. $^1$H NMR (300 MHz, CDCl$_3$) δ: 1.45 (s, 9H), 4.37 (d, J=6.3 Hz, 2H), 4.86 (br s, 1H), 7.42 (d, J=8.1 Hz, 2H), 7.83 (d, J=8.1 Hz, 2H), 9.98 (s, 1H).

{[4-(tert-Butoxycarbonylamino-methyl)-phenyl]-hydroxy-methyl}-phosphonic acid diethyl ester (8): A mixture of 7 (1.55 g, 6.6 mmol), diethyl phosphite (850 μl, 6.6 mmol) and triethylamine (930 μl, 6.6 mmol) in benzene (5 ml) was refluxed in an oil bath (75-80° C.) for 50 hours. The completion of the reaction was judged by observing the disappearance of the aldehyde peak at 9.98 ppm using NMR spectroscopy. The solvent was evaporated and the product, obtained as a racemic mixture, was purified by flash chromatography using 5% triethylamine in ethyl acetate ($R_f$=0.45) in 83% yield. $^1$H NMR (300 MHz, CDCl$_3$) δ: 1.21-1.29 (m, 6H), 1.46 (s, 9H), 3.17 (br s, 1H), 3.94-4.17 (m, 4H), 4.31 (d, J=5.1 Hz, 2H), 4.85 (br s, 1H), 4.95 (d, J=11 Hz, 1H), 7.26 (d, J=7 Hz, 2H), 7.45 (d, J=7 Hz, 2H)

{Bromo-[4-(tert-butoxycarbonylamino-methyl)-phenyl]-methyl}-phosphonic acid diethyl ester (9): To an ice cold solution of 8 (2.0 g, 5.5 mmol) in pyridine (0.82 ml) and acetonitrile (11 ml) was added dibromotriphenyl phosphorane (3.1 g, 7.3 mmol) and the reaction mixture was stirred on ice for 1.5 hours, followed by 2 hours at room temperature (Gajda, 1990). The solvent was rotary evaporated and the crude was dried on pump overnight. The crude was triturated with ethyl acetate and hexane mixture (7:3) and the white cake was filtered off on a sintered funnel. The cake was washed twice with 5 ml solvent and the filtrate was concentrated by flushing air prior to loading on the column. Purification by flash chromatography using ethyl acetate and hexane (7:3) mixture ($R_f$=0.5) gave the product 9 as an oil in 51% (1.21 g) yield. $^1$H NMR (300 MHz, CDCl$_3$) δ: 1.17 (t, J=7.2, 3H), 1.34 (t, J=7 Hz, 3H), 1.46 (s, 9H), 3.85-4.2 (m, 4H), 4.3 (d, J=6 Hz, 2H), 4.84 (d, J=13 Hz, 1H), 7.26 (d, J=7.2 Hz, 2H), 7.45 (d, J=7 Hz, 2H).

[(4-Aminomethyl-phenyl)-bromo-methyl]-phosphonic acid diethyl ester (10): To an ice cold solution of 9 (1.21 g, 2.8 mmol) in methylene chloride (14 ml) was added trifluoroacetic acid (TFA) neat (12 ml) and the reaction mixture was stirred at room temperature for 15-20 minutes. After the volatile components were removed on pump for about 5 hours, the crude was dissolved in methylene chloride (60 ml) and washed with cold saturated sodium bicarbonate (60 ml) solution. The aqueous layer was extracted in 2×60 ml methylene chloride. The organic layers were combined, dried on anhydrous sodium sulfate and evaporated to dryness (crude 0.8 g). The crude obtained was used further in the next step of synthesis without any further purification. $^1$H NMR (300 MHz, CDCl$_3$) δ: 1.25 (t, J=7 Hz, 3H), 1.35 (t, J=7 Hz, 3H), 3.9-4.2 (m, 6H), 4.8 (d, J=13 Hz, 1H), 7.4 (d, J=8 Hz, 2H), 7.48 (d, J=8 Hz, 2H), 8.1 (br s, 2H).

[Bromo-(4-{[6-(2-oxo-hexahydro-thieno[3,4-d]imidazol-6-yl)-hexanoylamino]-}-phenyl)-methyl]-phosphonic acid diethyl ester (11): To a solution of 10 (0.85 g, 2.53 mmol) in anhydrous DMF (20 ml) under argon atmosphere, was added (+)Biotinamido-N-hydroxysuccinimide ester (0.0.92 g, 2.7 mmol) all at once and the reaction mixture was stirred vigorously at room temperature for about 72 hours. DMF was removed on rotary evaporator and the crude was further dried on vacuum pump for 48 hours. This crude was used directly in the next step of synthesis.

[Bromo-(4-{[5-(2-oxo-hexahydro-thieno[3,4-d]imidazol-6-yl)-pentanoylamino]-methyl}-phenyl)-methyl]-phosphonic acid (I): To an ice-cold solution of 11 (0.04 g, 0.072 mmol) in anhydrous DMF (0.7 ml) under argon atmosphere, was added all at once bromotrimethylsilane (McKenna et al., 1977) (130 μl of 97% solution, 0.72 mmol) solution and the reaction mixture was stirred at room temperature for 18 hours. The volatile components of the reaction mixture were carefully removed on rotary evaporator under reduced pressure without any heating. After the resulting brown oil was stirred at room temperature for 2 hours with 90% methanol/water mixture (1.5 ml), the methanol was rotary evaporated and the resulting solution was brought to pH 7-7.5 using saturated sodium bicarbonate solution. The mixture was lyophilized and the purification of the final product (1) was achieved on HPLC ($R_f$=32.6 minutes) using a preparative C-18 column with a linear gradient of mobile phase water (solvent A) and acetonitrile (solvent B), containing 0.1% TFA. The appearance of the various fractions were monitored at 260 nm on a UV detector coupled to HPLC. $^1$H NMR (300 MHz, DMSO) δ: 1.26-1.58 (m, 6H), 2.1 (t, J=7.2 Hz, 2H), 2.51 (d, J=12 Hz, 1H), 2.73-2.80 (dd, J=12.3 Hz, 5.1 Hz, 2H), 3.04 (m, 1H), 4.05 (m, 1H), 4.16 (s, 2H), 4.23 (m, 1H), 5.02 (d, J=12 Hz, 1H), 6.36 (brs, 1H), 7.12 (d, J=8 Hz, 2H), 7.44 (d, J=8 Hz, 2H), 8.24 (t, J=6 Hz, 1H); MS (ESI+): m/z calculated for ($C_{18}H_{25}BrN_3O_5PS$+1) 506 (100%) 508 (98%); Found 506 (100%) and 508 (98%).

{Bromo-[4-({6-[5-(2-oxo-hexahydro-thieno[3,4-d]imidazol-6-yl)-pentanoylamino]-hexanoylamino}-methyl)-phenyl]-methyl}-phosphonic acid diethyl ester (12): This was essentially prepared following the same methodology as used in the synthesis of 11 with the exception that (+) Biotinamidohexanoic acid N-hydroxysuccinimide ester was used instead in the coupling with 10. The partial purification of the crude using flash chromatography on silica gel ($R_f$=0.3) with 10% methanol in methylene chloride gave a glue-like solid in 60% (0.06 g) yield which was used then in the final step of synthesis. (Caution: The crude product decomposes upon standing in silica gel as evident by thin layer chromatography). At this stage, the right product was ensured by characterization using ESI-MS for the molecular ion. MS (ESI+): m/z calculated for ($C_{28}H_{44}BrN_4O_6PS$+1) 675.2 (100%) 677.2 (98%); Found 675.2 (100%) and 677.2 (98%).

{Bromo-[4-({6-[5-(2-oxo-hexahydro-thieno[3,4-d]imidazol-6-yl)-pentanoylamino]-hexanoylamino}-methyl)-phenyl]-methyl}-phosphonic acid (II): This was prepared and purified again essentially following the protocol used in the synthesis of I. $^1$H NMR (300 MHz, DMSO) δ: 1.2-1.7 (m, 16H), 2.2 (t, J=5 Hz, 2H), 2.6 (d, J=12 Hz, 1H), 2.71-2.82 (dd, J=12.3 Hz, 5.1 Hz, 2H), 3.1 (m, 1H), 4.15 (m, 1H), 4.24 (s, 2H), 4.32 (m, 1H), 5.1 (d, J=12 Hz, 1H), 6.46 (brs, 1H), 7.2 (d, J=8 Hz, 2H), 7.5 (d, J=8 Hz, 2H) 7.75 (br t, 1H), 8.3 (br t, 1H), MS (ESI+): m/z calculated for ($C_{24}H_{36}BrN_4O_6PS$+1) 619.13 (98%) 621 (100%); Found 619 (98%) and 621 (100%).

PTPs and Non-PTP Proteins. Recombinant PTPs were expressed and purified as described (Sun et al., 2003). Non-PTP enzymes were primarily purchased from Sigma-Aldrich and stored at −20° C. Calpain was purchased from Calbiochem Inc. and stored at 4° C. PP2B was a generous gift from Dr. Frank Rusnak. Grb2-SH2 domain (54-164) fusion protein and thermolysin from *Bacillus thermoproteolyticus rokko* were purchased from Santa Cruz Biotech. Inc. and Sigma, respectively. SHC-PTB domain (residues 17-203) and SNT1-PTB domain (residues 11-140) proteins were generous gifts from Prof. M-M Zhou.

Kinetic Characterization of PTP Inactivation by the BBP-based Probes. PTP inactivation by the BBP-based probes was studied at 25° C. in a pH 6 buffer containing 50 mM sodium succinate, 1 mM EDTA, 1 mM DTT, and ionic strength of 150 mM adjusted with NaCl. The inactivation reaction was initiated by the addition of a 5 µl aliquot of PTP stock to a 45 µl solution containing appropriately diluted 1 (final DMSO 5%). At appropriate time intervals, aliquots of 2 µl were removed from the reaction and added into a 200 µl solution containing 20 mM p-nitrophenyl phosphate (pNPP) in pH 6.0 buffer at 30° C. (Sun et al., 2003). The kinetic parameters of the inactivation reaction were obtained by fitting the data to the following equations:

$$\frac{A_t}{A_0} = \frac{A_\infty}{A_0} - \left(\frac{A_0 - A_\infty}{A_0}\right)e^{-k_{obs} \cdot t} \quad \text{(Equation 1)}$$

$$k_{obs} = \frac{k_i \times [I]}{K_I + [I]} \quad \text{(Equation 2)}$$

Covalent Labeling with the PTP Probes. In a typical labeling experiment, the reaction was initiated by adding the PTP probe (final concentration 1 mM) to the preincubated enzyme (final concentration 25 µM) in appropriate buffer at 25° C. for 1 hour, unless otherwise stated. All labeling reactions involving PTPs were carried out in 50 mM sodium succinate buffer (pH 6.0) that contained 1 mM EDTA, 1 mM DTT and adjusted to the ionic strength of 150 mM with NaCl. Labeling reaction involving non-PTP enzymes were carried out in their respective optimum activity conditions and thus the following buffers, adjusted to the ionic strength of 150 mM, were used: alkaline phosphatase, 50 mM Tris, pH 9.0, 1 mM $MgCl_2$; potato and prostatic acid phosphatases, 100 mM sodium acetate, pH 5.0, 1 mM EDTA; protein phosphatase 1 and λ phosphatase, 50 mM 3,3-dimethylglutarate, pH 7.0, 2 mM $MnCl_2$; papain and lysozyme, Grb2-SH2, Shc-PTB, and SNT1-PTB, 50 mM 3,3-dimethylglutarate, pH 7.0, 1 mM EDTA; calpain, 100 mM imidazole, pH 7.3, 10 mM $CaCl_2$, 1 mM DTT; glyceraldehyde-3-phosphate dehydrogenase, 15 mM sodium pyrophosphate, pH 8.5, 7.5 mM NAD, 1 mM DTT; chymotrypsin, 50 mM Tris, pH 7.8, 50 mM $CaCl_2$; trypsin, 100 mM Tris, pH 8.5, 1 mM EDTA; bovine serum albumin, 50 mM sodium succinate buffer, pH 6.0, 1 mM EDTA, 1 mM DTT; protein phosphatase 2B, 50 mM 3,3-dimethylglutarate, pH 7.0, 0.3 µM calmodulin, and 2 mM $MnCl_2$; Src kinase, 100 mM Tris, pH 7.0, 1 mM EDTA; thermolysin, 50 mM HEPES, pH 7.0, 5 mM $CaCl_2$; GST, 50 mM 3,3-dimethylglutarate, pH 7.0, 1 mM EDTA, and 1 mM DTT.

Western Blot Analyses of the Labeling Reaction. The labeling reactions were quenched by the addition of 1 volume of 2×SDS loading buffer (reducing) at 75° C. for 5 minutes. Each sample was divided into two equal halves, which were separated on a 12.5% SDS-PAGE (3 µg protein/lane). The proteins from one gel were transferred overnight to a nitrocellulose membrane at 4° C. The membrane was then blocked with 5% nonfat dry milk in Tris-buffered saline (TBS) with 1% Tween (TBS-T) for 1 hour at 25° C. After two quick washes with TBS-T, the membrane blot was treated for 2 hours with anti-biotin-HRP conjugate (Cell Signaling Tech., 1:1000 dilution) in TBS-T containing 5% nonfat dry milk at 25° C. The anti-biotin-HRP treated blot was then washed three times (30 minutes each) with TBS-T and subsequently treated with HRP-substrate for 1 minute before exposing the chemiluminescent membrane blot to the film. The second gel was Coomassie-stained for protein visualization. In the labeling experiment involving YopH and its mutants (FIG. 6), the blot itself was stripped with stripping buffer (100 mM 2-mercaptoethanol and 2% SDS in 62.5 mM Tris-HCl, pH 6.7) for 30 minutes at 50° C. to remove the anti-biotin-HRP and HRP substrate. The blot was washed quickly a few times with water and exposed to Coomassie Blue for protein staining.

MALDI-TOF Mass Spectrometry. To prepare the modified YopH for MALDI-TOF experiment, 1 µM YopH was mixed with 10 mM PTP probe I. YopH alone with pH 6 succinate buffer was used as a control. After a 3-hour incubation at 25°

C., 10 μl sample was desalted by a ZipTip C4 column (Millipore) and eluted in 4 μl 50% acentonitrile/0.1% TFA. After mixing 1 μl of the elute with 1 μl saturated sinapinic acid solution (50% acentonitrile/0.1% TFA), a 1 μl aliquot was transferred to a 100 well MALDI sample plate (Applied Biosystems). Mass spectra were recorded on a Voyager-DE STR Biospectormetry-workstation (Applied Biosystems) in the positive polarity mode. All spectra are summations of 100 individual laser shots.

Results and Discussion

Given the large number and complexity of PTPs in cell signaling, new strategies are needed for the integrated analysis of PTPs in the whole proteome. The ability to profile the entire PTP family on the basis of changes in their activity should greatly accelerate both the assignment of PTP function and the identification of potential therapeutic targets. However until now, class-selective probes for PTPs were not available. The suicide substrate, 4-fluromethylaryl phosphate, was recently explored as a PTP probe (Lo et al., 2002), as hydrolysis of 4-fluoromethylaryl phosphate generates a highly reactive quinone methide intermediate, which can alkylate nucleophilic side chains at, or near, the phosphatase active site (Myers & Widlanski). Unfortunately, 4-flurom-ethylaryl phosphate is not specific for PTPs, as it also forms covalent adduct with other classes of phosphatases such as nonspecific prostatic acid phosphatase and protein Ser/Thr phosphatase calcineurin (Myers & Widlanski, 1993; Wang et al., 1994; Born et al., 1995). An additional drawback to this type of chemistry is that the diffusible, unmasked quinone methide electrophile could alkylate other proteins in the vicinity that carry nucleophilic residues on their surface. Consequently, chemical probes based on 4-fluromethylaryl phosphate lack the specificity required for global analysis of the PTPs superfamily. In the following, we describe the development of two specific activity-based PTP probes based on α-bromobenzylphosphonate (BBP, FIG. 1), a quiescent affinity inactivator of the *Yersinia* PTP YopH (Taylor et al., 1996).

Design and Synthesis of Biotinylated BBPs as Activity-Based PTP Probes. Ideally, an activity-based probe for the PTPs would consist of a PTP specific trapping device for covalent attachment to the enzyme active site and a linker that connects the trapping device with a reporter/affinity tag for visualization and purification. With this in mind, our first generation PTP probes I and II (FIG. 1) consist of a potential PTP specific affinity agent BBP, a linker, and a biotin tag. Compound II differs from I in that an additional hexanoic acid spacer is inserted between BBP and biotin. This was designed to evaluate whether the linker space between BBP and the biotin tag in I is sufficient to prevent steric hindrance that could block accessibility of BBP for PTP labeling or of the tag for detection and purification. One important aspect of the design involved separating the amine functionality at the 4 position of the phenyl ring by a methylene linker for subsequent condensation of (+) biotinamido-N-hydroxysuccinim-ide ester or (+) biotinamidohexanoic acid N-hydroxysuccin-imide ester, so as to avoid the undesirable in-situ elimination of the bromide leaving group during the synthesis.

The chemical synthesis of PTP probes I and II involved synthesizing a common intermediate 10 in a 7-step procedure (Scheme 1) and its subsequent coupling with the biotin-NHS ester analogues, followed by the deprotection of the phosphonate diethyl ester (Scheme 2). Thus, 4-cyanobenzyl bromide 3 was hydrolyzed in the presence of barium carbonate to produce 4-cyanobenzyl alcohol 4, which was subsequently reduced with lithium aluminum hydride under strict argon atmosphere to yield 4-hydroxymethyl-benzyl-ammonium chloride 5, upon acidic aqueous extraction (17). The amine functionality of 5 was then first masked by t-butyl carbamate to render (4-hydroxymethyl-benzyl)carbamic acid tert-butyl ester 6 (Far et al., 2002). Corey oxidation (Corey & Suggs, 1975) with pyridinium chlorochromate/sodium acetate gave the reactive aldehyde 7. The condensation of 7 with diethyl phosphite in the presence of triethylamine produced {[4-(tert-butoxycarbonylamino-methyl)-phenyl]-hydroxy-methyl}-phosphonic acid diethyl ester 8 as a racemic mixture. This racemic mixture of 8 was used as such in the following step of the synthesis. Bromination of the secondary alcohol, 8, to yield 9 was achieved using dibromotriphenyl phosphorane in pyridine (Gaida, 1990). Finally, deprotection of t-butyloxy-carbonyl with neat trifluoroacetic acid gave [(4-aminom-ethyl-phenyl)-bromo-methyl]-phosphonic acid diethyl ester (10). The coupling of 10 with (+) biotin N-hydroxysuccinim-ide ester (for I) and (+) biotinamidohexanoic acid N-hydrox-ysuccinimide ester (for II) in DMF gave 11 and 12 respectively. The phosphonate diesters (11 & 12) were deprotected with bromotrimethylsilane in DMF to yield I and II (McKenna et al., 1977).

Compounds I and II Are Active Site-Directed and Irreversible Inactivators of PTPs. To characterize I and II as activity-based PTP probes, we first examined for their effect on PTP activity using pNPP as a substrate. As expected, compound I inactivated the *Yersinia* PTP, YopH, in a time- and concentration-dependent first order process (data not shown). Similar results were obtained with several PTPs, including PTP1B, HePTP, SHP2, LAR, PTPα, PTPH1, VHR, and Cdc14. In addition, I and II were equally effective at inhibiting PTP activity, indicating that the linker size does not affect the probe reactivity. Thus, unless indicated otherwise, all subsequent experiments were performed with compound I due to its better solubility in aqueous solution. Inactivation of PTPs with I appeared irreversible as extensive dialysis and/or buffer exchange of the reaction mixture failed to recover enzyme activity.

Figure 2:
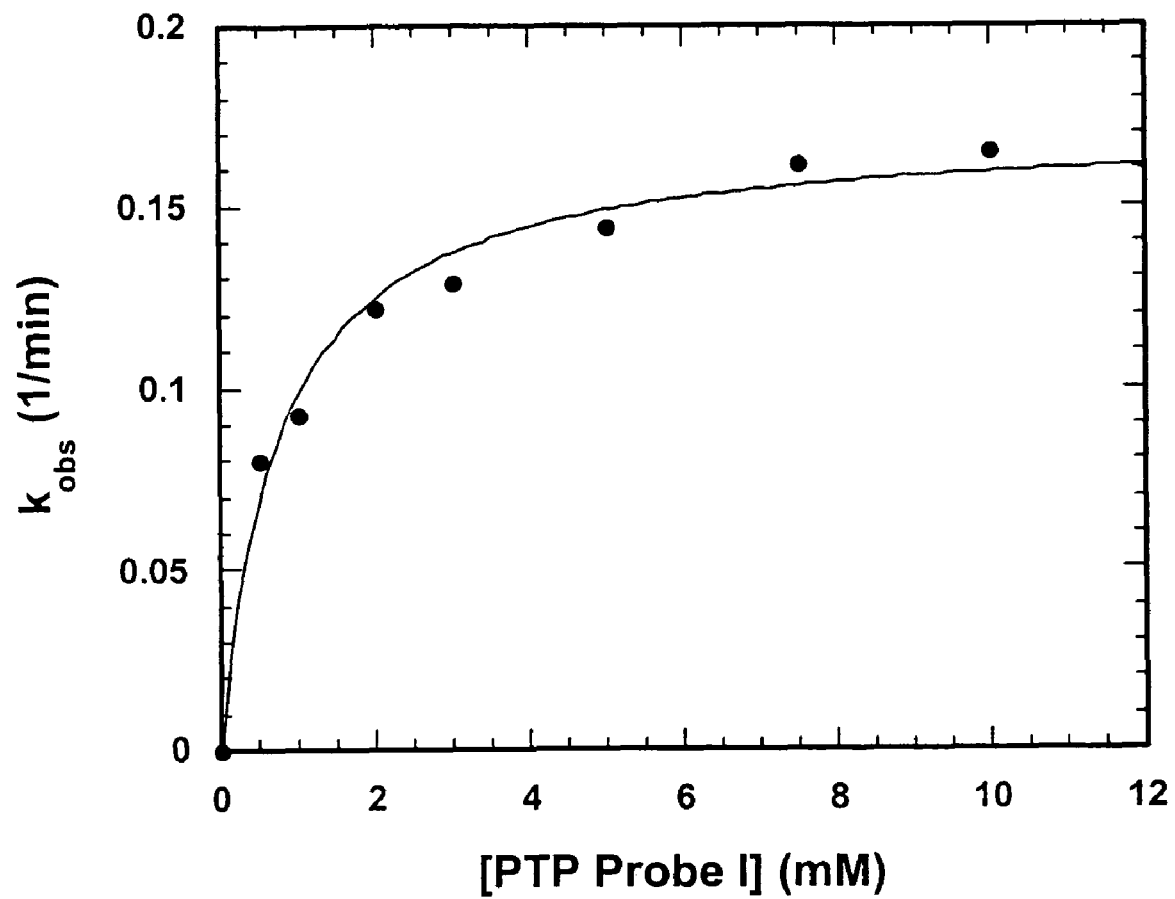
FIG. 2 is a graph of the concentration dependence of the pseudo-first-order rate constants $k_{obs}$ for compound I-mediated YopH inactivation. The curve was generated by fitting the data to Equation 2.

Analysis of the pseudo-first-order rate constant as a function of reagent concentration showed that compound I-mediated YopH inactivation displayed saturation kinetics (FIG. 2), yielding values for the equilibrium binding constant $K_I$ and the inactivation rate constant $k_i$ of 0.74 mM and 0.17 min$^{-1}$, respectively. Similar saturation kinetics was also observed for YopH inactivation by BBP ($K_I$=4.1 mM and $k_i$=0.11 min$^{-1}$). These results suggest that the BBP-based probes are active site-directed affinity agents whose mode of action likely involves at least two steps: binding to the PTP active site followed by covalent modification of active site residue(s). The ability of BBP-based probes to target PTP active site was expected because BBP mimics pTyr which is known to occupy PTP active site. Indeed, the $K_1$ values for I and BBP are similar to competitive inhibition constants measured for benzylphosphonate, a nonhydrolyzable pTyr mimetic (Sun et al., 2003). Further evidence in support of the inactivation being directed to the active site included that arsenate, a competitive PTP inhibitor, was able to protect PTP from BBP-mediated inactivation.

Compound I was quite stable in pH 6 buffers, although significant solvolysis could be detected at pH>7. To minimize any loss of the probe due to hydrolysis, subsequent labeling experiments were conducted at pH 6. It is however worth mentioning that the probe displayed similar reactivity toward the PTPs at both pH 6 and 7. Interestingly, prolonged incubation (48 hours) of I with 100 mM DTT, 50 mM azide or 50 mM cysteine in either pH 6 or 7 buffers did not produce the expected substitution products as evidenced by NMR and mass spectrometry. Moreover, these scavenging nucleophiles did not affect the rate of I-mediated PTP inactivation. These results demonstrate that the BBP-based probes are inert to nucleophilic agents and their propensity for rapid inactivation of PTPs suggests that a latent affinity group unleashes its reactivity only toward a suitably disposed nucleophilic residue in the active site.

Figure 3:
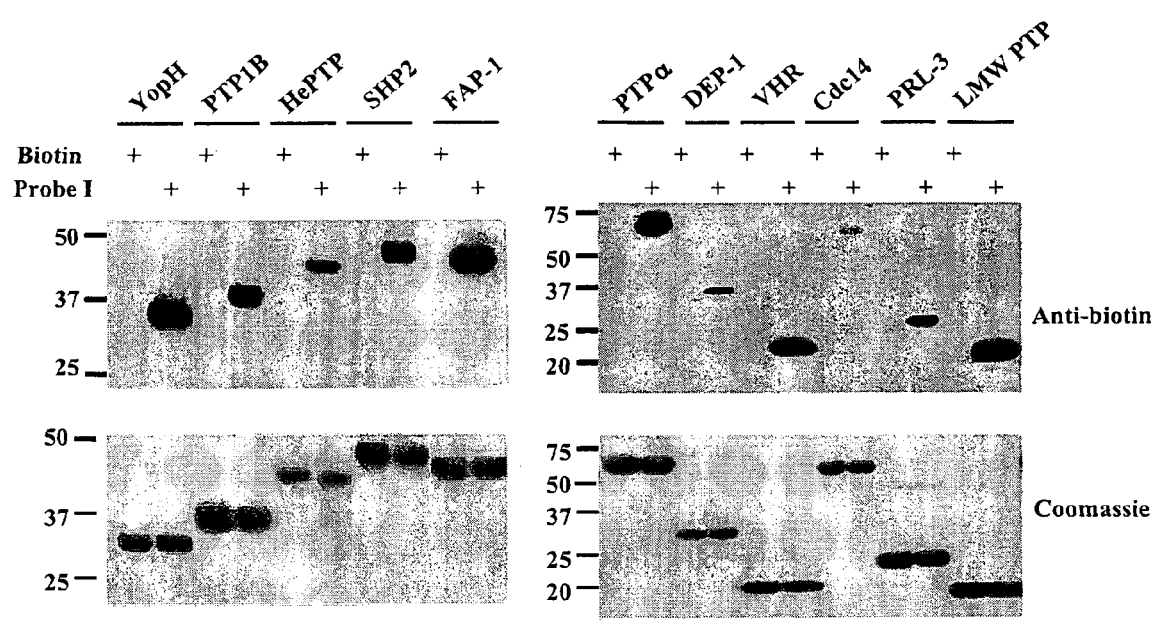
FIG. 3 is western- and Coomassie-stained blots showing the specific labeling of PTPs by I. PTPs (3 μg) were mixed with 1 mM of I in pH 6 buffer containing 50 mM succinate, 1 mM EDTA and ionic strength of 0.15 M at 25° C. for 1 hr. The reaction mixtures were separated by 10% SDS PAGE and subjected to western blotting analysis using anti-biotin-horseradish peroxidase conjugate. Bound anti-biotin antibodies were visualized by chemiluminescence using an ECL kit (Amersham-Pharmacia). Upper gels, ECL-developed; lower gels, Coomassie blue-stained.

Compounds I and II Form a Covalent Adduct with PTPs. To demonstrate that I and II inactivates PTPs by forming a covalent adduct with the enzymes, we incubated the PTP with either biotin or the probe at 1 mM concentration and pH 6 for 1 hour. The sample was divided into two halves and separated by SDS-PAGE. As shown in FIG. 3, covalent labeling of the PTP by the biotin-tagged probe was visualized with anti-biotin antibody-conjugated peroxidase chemiluminescence while the amount of loaded protein was determined by Coomassie blue staining. As expected, biotin alone did not label the PTPs while the biotin-tagged probe I was covalently incorporated into all PTPs tested, including cytosolic PTPs YopH, PTP1B, HePTP, SHP2, and FAP-1, receptor-like PTPs PTPα and DEP-1, dual specificity phosphatases VHR, Cdc14, and PRL3, and the low molecular weight PTP. Thus, compound I can react with a broad range of enzymes from the PTP superfamily. Furthermore, the amount of labeling correlated with PTP activity. Thus, it is possible that the probe can be used to analyze the activation status of PTPs under different physiological conditions. Again, similar results were obtained with II, indicating that the biotin tag has similar accessibility to the anti-biotin antibodies.

Figure 4:
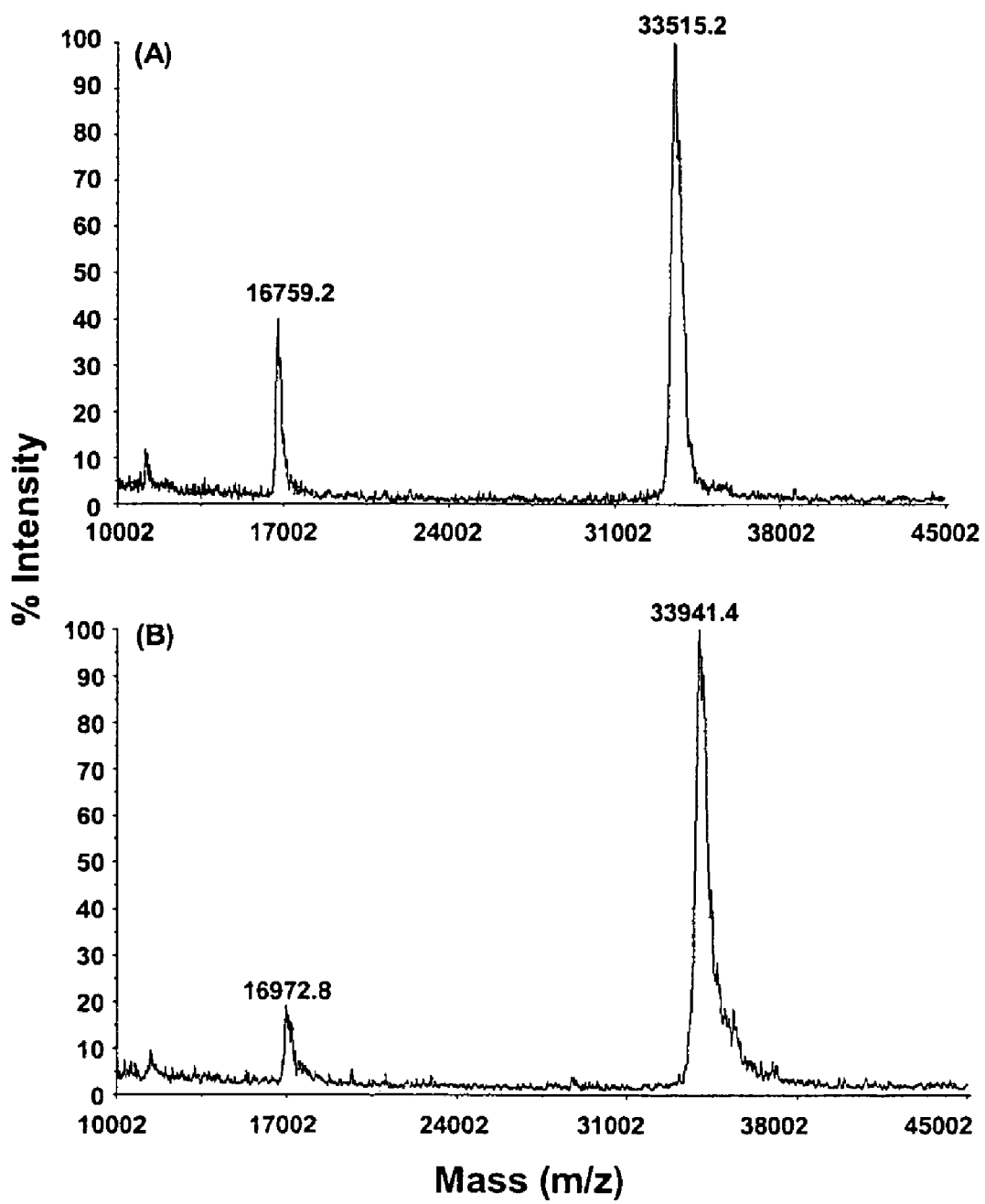
FIG. 4 shows MALDI-TOF mass spectra of YopH (A) and YopH labeled with I (B). The high-intensity peaks show the mass of the singly-charged proteins, and the low-intensity peaks are the doubly-charged proteins.
Figure 5:
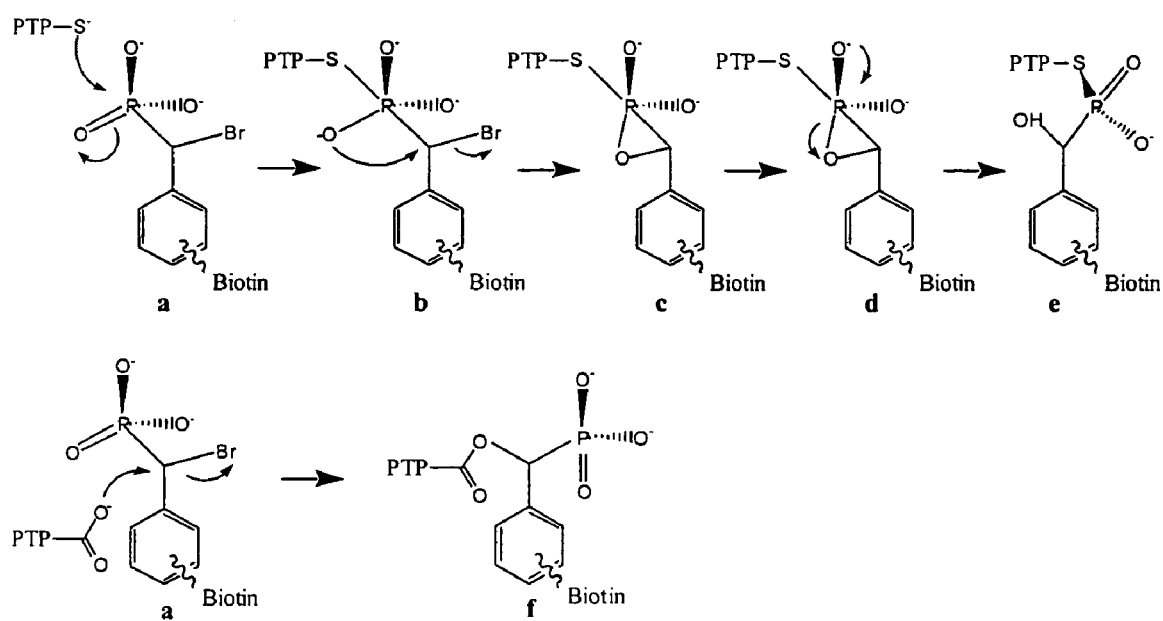
FIG. 5 is a diagram of potential mechanisms for PTP inactivation by the BBP-based probes.

To provide more direct evidence that the PTP probes can covalently label PTPs, we also analyzed the compound I treated YopH using MALDI (matrix-assisted laser desorption/ionization) mass spectrometry (FIG. 4). The measured $[M+H]^+$ value of 33515 for YopH agreed with the theoretical value. The measured $[M+H]^+$ value of 33941 for the modified YopH indicated a mass shift of 426, which corresponded exactly to the expected mass shift resulting from covalent attachment of I (mass 506) to YopH concomitant with a loss of bromide (mass 80) (FIG. 5). The absence of a peak at m/z 33515 indicated the high efficiency of the modification reaction.

Mechanism of PTP Inactivation by Compound I. The PTPs share a conserved active site that recognizes aryl phosphates and a common catalytic mechanism that utilizes a highly reactive nucleophilic Cys residue (Zhang, 2001). This Cys (Cys403 in YopH) displays an unusually low $pK_a$ of ~5 (Zhang & Dixon, 1993), and is situated at the bottom of the pTyr-binding pocket such that its Sγ atom is poised 3 Å from the phosphorus atom of pTyr (Sun et al., 2003). In the catalytic mechanism, the active site Cys initiates a nucleophilic attack on the phosphorus, leading to the formation of a thiophosphoryl enzyme intermediate. This is assisted by the general acid (Asp356 in YopH), which is in close proximity to the scissile phenolic oxygen of pTyr. The active site arginine (Arg409 in YopH) is involved in initial binding of the pTyr substrate and stabilizes the transition state.

If the BBP moiety binds the PTP active site in a manner similar to pTyr, it could covalently modify the PTP via two potential mechanisms (FIG. 5). In one mechanism, the active site Cys initiates nucleophilic attack, as in a normal substrate reaction, directly on the phosphonate group to give a transient phosphorane-like intermediate (b), followed by closure to a three-membered ring species (c) with the expulsion of the bromide. Subsequent ring opening produces α-hydroxylbenzylphosphonate covalently attached to the active site Cys (e). Alternatively, the strategically positioned Asp general acid could displace the bromide directly from the benzylic position to yield f. Both mechanisms will result in a covalent adduct with the net loss of a bromide.

Figure 6:
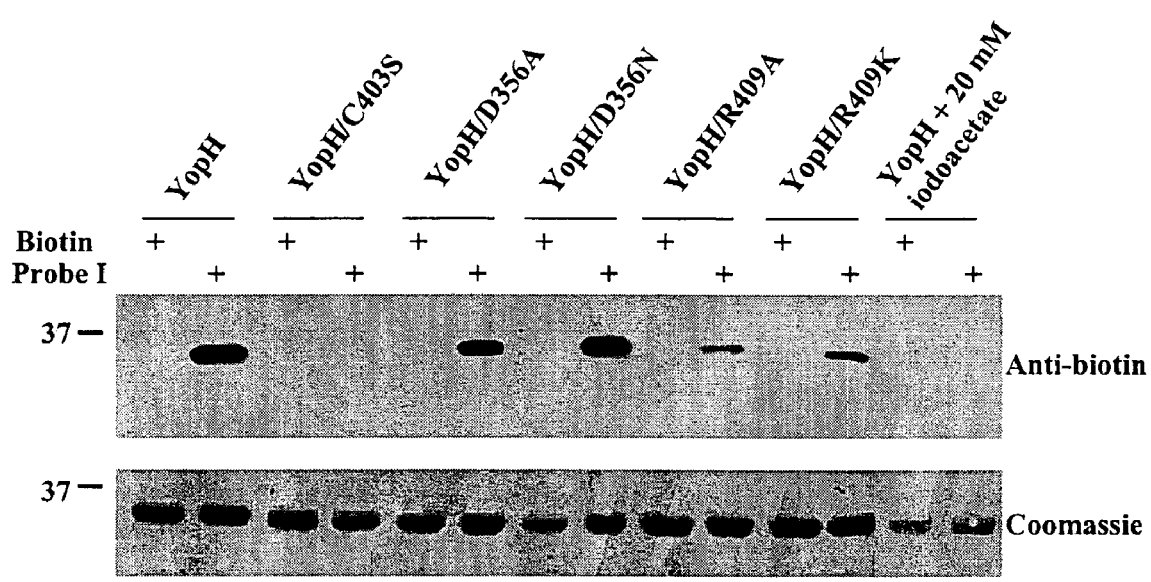
FIG. 6 is a western- and Coomassie-stained gel showing covalent labeling of wild-type and mutant YopH with PTP probe I.

To distinguish these possibilities, we carried out labeling experiments with several site-directed mutants of YopH. The C403S mutant is catalytically inactive but retains substrate-binding ability (Zhang et al., 2000). As seen in FIG. 6, C403S did not show any reactivity toward I. In addition, pretreatment of YopH with iodoacetate, which is known to specifically alkylate Cys403 (Zhang & Dixon, 1993), also blocked the incorporation of I into YopH. In contrast, incubation of the general acid deficient mutants D356A and D356N with I led to a complete loss of phosphatase activity (data not shown) with a comparative amount of labeling as that of the wild-type YopH. Together, the results exclude the involvement of Asp356 in displacing the bromide in a direct nucleophilic fashion, and strongly suggest that the thiol group of the active site Cys403 is the site of covalent attachment for the BBP-based probes. Consistent with the importance of the active site Arg in binding of the phosphoryl group in the substrate, a dramatic decrease in covalent labeling was observed for R409A and R409K. Moreover, more probe I was incorporated into R409K than R409A in accord with R409K's higher affinity for substrate than R409A (Zhang et al., 1994). Collectively, the results are consistent with a mechanism by which the activity-based probe is targeted to the PTP active site for covalent adduct formation that involves the nucleophilic Cys. Although our results do not formally exclude the possibility that the active site Cys may directly displace the bromide at the benzylic position, this is highly unlikely because in the crystal structures of PTP bound to pTyr or its nonhydrolyzable analogues, the benzylic position is out of reach to the Cys nucleophile.

Figure 7:
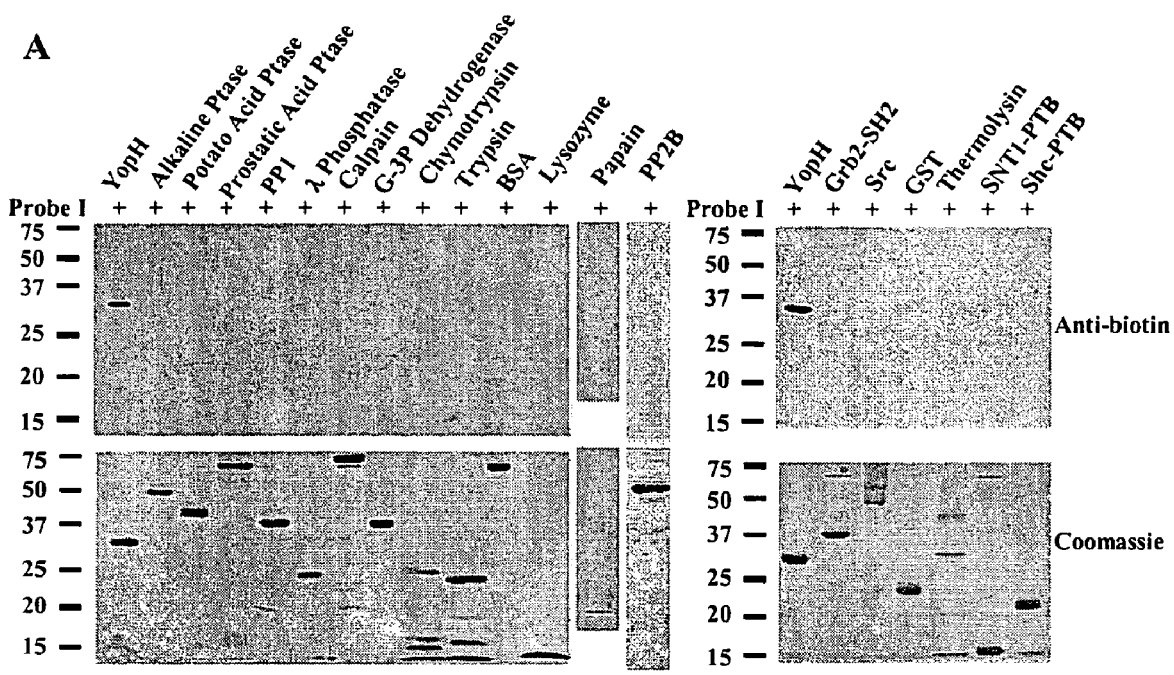
FIG. 7 is western- and Coomassie-stained gels showing the specificity of the PTP probe I. Panel A shows the activity of I toward non-PTP enzymes/proteins; Panel B shows the activity of I toward the total cell lysates from *E. coli*. The samples were treated with 1 mM I for 1 hour. The reaction mixtures were separated by 10% SDS PAGE and subjected to western blotting analysis using anti-biotin-horseradish peroxidase conjugate.
Figure 7:
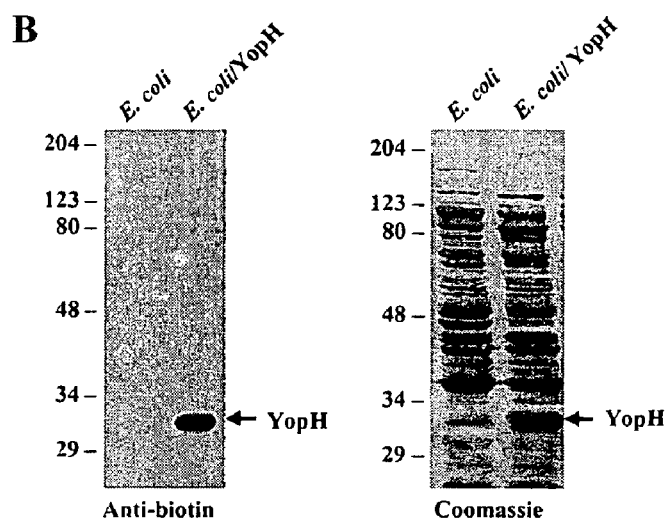

Compound I Is Highly Specific for PTPs. Since compound I was intended for PTP activity profiling at the whole proteome level, we wanted to determine if the probe exhibits cross-reactivity with other protein classes. To this end, we examined the reactivity of I towards a panel of non-PTP enzymes/proteins, including alkaline phosphatase, potato and prostatic acid phosphatases, Ser/Thr protein phosphatases PP1, PP2B, and γ phosphatase, the SH2 domain of Grb2, the PTB domains of Shc and SNT1, the Src kinase, serine proteases trypsin and chymotrypsin, metalloprotease thermolysin, cysteine proteases papain and calpain, glyceraldehyde 3-phosphate dehydrogenase and glutathione S transferase (both of which also possess reactive low $pK_a$ Cys), bovine serum albumin, and lysozyme. As shown in FIG. 7A, none of the proteins tested were reactive to compound I. The lack of reactivity of I toward non-phosphatases is easy to understand because these enzymes do not recognize aryl phosphates as substrates. Although SH2 and PTB domains bind pTyr, they lack reactive groups in the binding site and are inert to compound I. What is remarkable is that although both alkaline and acid phosphatases hydrolyze aryl phosphates and possess an active site nucleophile (Ser and His, respectively), neither could be labeled by the probe. The source of this specificity may relate to the highly reactive active site Cys in PTPs and the special affinity of the nucleophilic sulfur for phosphorus.

Figure 8:
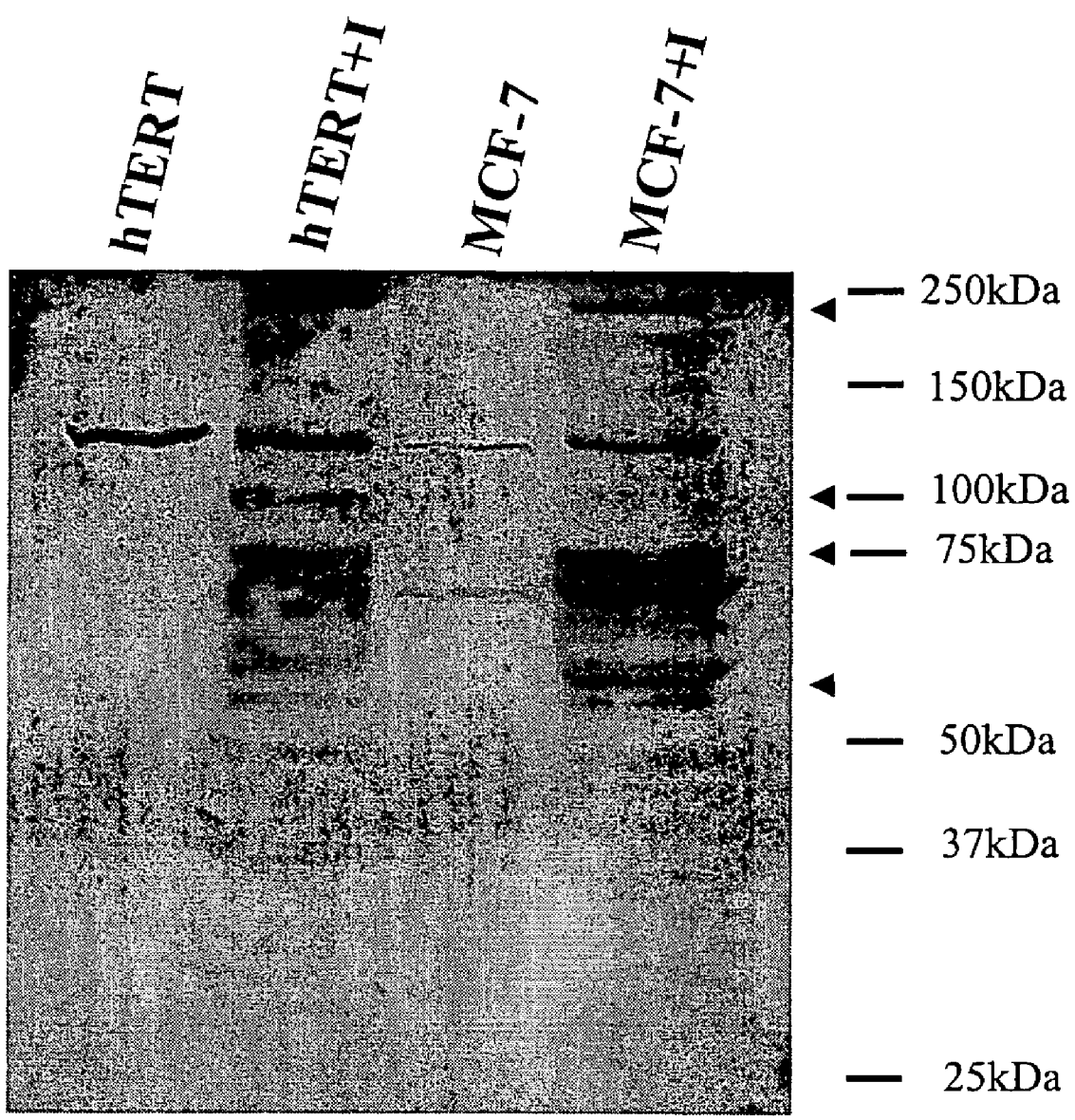
FIG. 8 is an immunoblot of a global analysis of PTP activity with compound I in normal and cancer breast cells. MCF-7 or hTERT cells were lysed in 50 mM MES, pH 6.0, 150 mM NaCl, 1% Triton X-100, 10% glycerol, 5 mM EDTA, 1 µg/ml aprotinin, 1 µg/ml leupeptin, 1 mM PMSF, and incubated with 1 mM compound I for 1 hr at room temperature. 50 µg protein was loaded to and separated by 10% SDS-PAGE. Biotinylated proteins were detected by immunoblotting using anti-biotin antibody.

To further evaluate the specificity of compound I for PTPs, we also incubated I with the total cell lysates from *E. coli* transformed with or without YopH. Western-blot analysis of the reaction mixture indicated that, with the exception of YopH, no *E. coli* proteins were labeled by the probe (there are no PTPs in *E. coli*) (FIG. 7B). This level of selectivity indicates that compound I is suitable for global analysis of PTP activity in a cell. As initial proof-of-principle, we tested the hypotheses that the activity of PTPs can be significantly altered in cancer cells, and that the activity-based probes are capable of profiling PTP activity at the whole proteome level. We performed a preliminary experiment with a normal human breast cell line hTERT and a human breast cancer cell line MCF-7. As shown in FIG. 8, there are at least four PTPs (marked by arrows) displaying significant different activities between these two cell lines. Two PTPs (230 and 100 kDa) showed decreased activities in MCF-7 cells than those in hTERT cells. In contrast, the activities of two PTPs migrating at 60 and 75 kDa were dramatically higher in MCF-7 cells than those in hTERT cells. In fact, the 60 kDa band may represent a PTP whose expression is induced in MCF-7 cells.

Experiments are carried out to further optimize the reaction conditions with mammalian cell lysates and to identify the PTPs with altered activity in MCF-7 cells. This is accomplished by affinity capture of the biotin-tagged PTPs with avidin column followed by LC/MS/MS analysis. We were able to identify PTP1B from the protein pool eluted with biotin from the avidin column using PTP1B antibody, and we estimated that under our conditions, the probe could detect PTP1B in the sub nanogram range, quantities sufficient for mass spectrometry experiments. We note that there are a couple of nonspecific bands in the non-treated cell lysates (FIG. 8), which may be due to endogenous biotinylated proteins. If this represents a serious problem for PTP identification, the cell lysate can be pre-cleared with anti-biotin antibodies before treatment with the PTP probe. Identification of PTPs whose activities are abnormally regulated in cancer cells may establish links between members of the PTP family and cancer.

In summary, we described the design and synthesis of two activity-based PTP probes that consist of a PTP specific trapping device, α-bromobenzylphosphonate, for covalent attachment to the PTPs and a linker that connects the trapping device with a biotin tag for visualization and purification. We showed that the probes inactivate a broad range of PTPs in a time- and concentration-dependent fashion. We established that this inactivation is active site-directed and irreversible. We provided evidence that these probes form covalent adduct with PTPs, mostly likely involving the active site Cys residue. More importantly, we demonstrated that the probes exhibit extremely high specificity toward PTPs while remaining inert to other enzymes/proteins, including the whole proteome from *E. coli*. These properties indicate that the activity-based PTP probes can be used to profile PTP activities in both normal and pathological conditions, enabling direct isolation and identification of PTP activity in distinct physiological states.

Example 2

Fluorescent-Based PTP Probes

Example Summary

In continuation of our efforts to develop activity-based probes for protein tyrosine phosphatases, fluorescent-based activity-based probes were developed. Two main advantages of such fluorescent-based activity-based probes are that (i) these probes are ultra sensitive and (ii) the analysis precludes the need for antibody-based detection, which can be rather cumbersome. The general structure of the probe is as shown in Formula B:

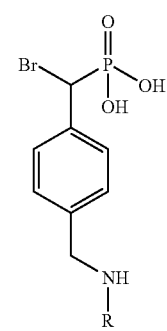

where R is a fluorescent moiety.

More specifically, the following two fluorophores were incorporated and tested: (a) Lissamine™ Rhodamine B (b) Cy 5. The structure of these two probes is shown in FIG. 9.

These fluorescent-based PTP probes can be used to detect active PTPs in complex proteomic mixtures and are at least 1000-fold more sensitive than antibody-based probes.

Experimental Procedures

Synthesis of Lissamine™ Rhodamine B and Cy5 Based PTP Probes. The following protocols were adopted for synthesis of the fluorescent probes.

Synthesis of [(4-Aminomethyl-phenyl)-bromo-methyl]-phosphonic acid diethyl ester: This compound was prepared in the following way, with a slight modification of the protocol published elsewhere (Kumar et al., 2004). Thus, in a round bottom flask, {Bromo-[4-(tert-butoxy-carbonylamino-methyl)-phenyl]-methyl-phosphonic acid diethyl ester (0.24 g, 0.56 mmol) (Kumar et al., (2004)) was dissolved in methylene chloride (5 ml) and chilled on ice. To this, was added trifluoroacetic acid (TFA) (99%, 3 ml) and the reaction mixture was stirred vigorously on ice. The duration of the reaction (typically about 20 minutes) was monitored by following the disappearance of starting material on thin layer chromatography plate. After the reaction was over, TFA was rapidly removed on rotary evaporator and subsequently on high vacuum. The resulting brown crude was suspended in methylene chloride (20 ml) and washed with cold saturated sodium bicarbonate (20 ml) solution. The aqueous layer was extracted in 3×20 ml methylene chloride. The combined organic layers were dried on anhydrous sodium sulfate and evaporated to dryness on high vacuum. The crude (0.16 g) which appeared pure, based on NMR, was directly used in the next step of synthesis. $^1$H NMR (300 MHz, CDCl$_3$) δ: 1.25 (t, J=7 Hz, 3H), 1.35 (t, J=7 Hz, 3H), 3.9-4.2 (m, 6H), 4.8 (d, J=13 Hz, 1H), 7.4 (d, J=8 Hz, 2H), 7.48 (d, J=8 Hz, 2H), 8.1 (br s, 2H)

Synthesis of Lissamine™ Rhodamine B-PTP Sensor: This compound was prepared by condensing the Lissamine™ rhodamine B sulfonyl chloride (mixed position 2 and 4 isomers; Molecular Probes Inc.) with [(4-Aminomethyl-phenyl)-bromo-methyl]-phosphonic acid diethyl ester. Thus, to a solution of [(4-Aminomethyl-phenyl)-bromo-methyl]-phosphonic acid diethyl ester (100 mg, 0.30 mmol) in DMF (1.0 ml) was added sequentially Lissamine™ rhodamine B sulfonyl chloride (206 mg, 0.36 mmol) and triethylamine (60 mg, 0.6 mmol), and the reaction mixture was stirred at room temperature for 24 hours in an inert atmosphere of argon. After the solvent was completely removed on high vacuum, the crude reaction mixture, that contained the condensed intermediate, as detected by ESI-MS, was treated in the following way. Thus, to an ice-cooled reaction mixture of crude in DMF (0.5 ml) was added trimethylsilylbromide (460 mg, 3 mmol) in drops and allowed to react at room temperature for 24 hr. The volatiles were removed on a rotary evaporator and the reaction mixture was stirred in the presence of 9:1 methanol/water (10 ml) for 2 hr. A purification of the crude by reverse phase semi-preparative HPLC (a linear gradient of 0.1% TFA in acetonitrile and water) yielded the final product as two separate 2 and 4 positional isomers (26% yield). The characterization of both positional isomers was achieved using ESI-MS (+): m/z calculated for ($C_{35}H_{40}BrN_3O_9PS_2$+1) 822.11 (100%), 820.11 (94%), 823.11 (41%); found 822.17 (100%), 820.14 (94%), 823.23 (41%).

Synthesis of Cy5-PTP sensor: A solution of Cy5 mono n-hydroxysuccinimide ester (10 mg, 0.013 mmol) and [(4-Aminomethyl-phenyl)-bromo-methyl]-phosphonic acid diethyl ester, (4.2 mg, 0.013 mmol) in DMF (0.5 ml) was stirred in an argon atmosphere for 74 hours. The solvent was evaporated on high vacuum for a couple of nights and the resulting solid was re-suspended into DMF (0.4 ml) and chilled on ice. To this was added trimethylsilylbromide (49 mg, 0.324 mmol) in drops and the resulting mixture was allowed to react at room temperature for 24 hr. The volatiles were removed on a rotary evaporator and the reaction mixture was stirred in the presence of 9:1 methanol/water (2 ml) for 2 hr. A purification of the crude by reverse phase semi-preparative HPLC (a linear gradient of 0.1% TFA in acetonitrile and water) yielded the final product in 61% yield. The characterization was achieved by ESI-MS; m/z calculated for ($C_{41}H_{50}BrN_3O_{10}PS_2$+1): 920.18 (100%), 918.19 (94%), 921.19 (47%); found 920.16 (100%), 918.06 (94%), 921.18 (47%)

Results and Discussion

Figure 10:
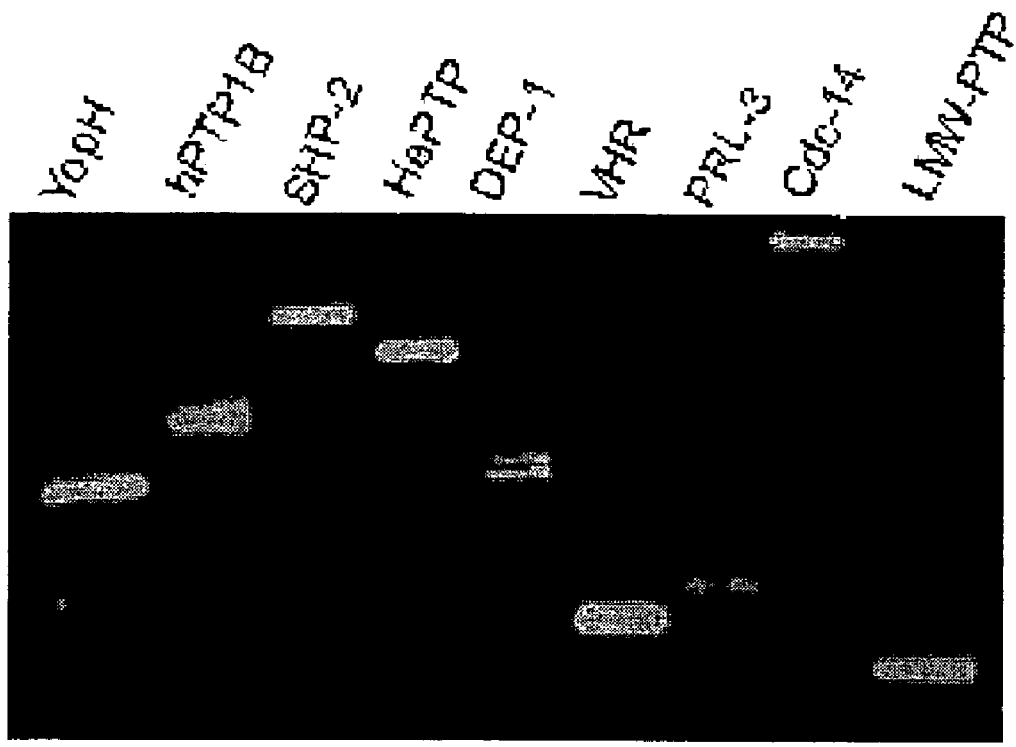
FIG. 10 shows the results of labeling experiments with PTPs. (Panel A) Activity-based labeling of a panel of PTPs by the Lissamine™ rhodamine B-PTP probe as detected by scanning the gel containing labeled protein on a Typhoon 9400 scanner. (Panel B) Silver-stained gel depicting the protein amount. The protein amount used in each lane was 10 ng.
Figure 10:
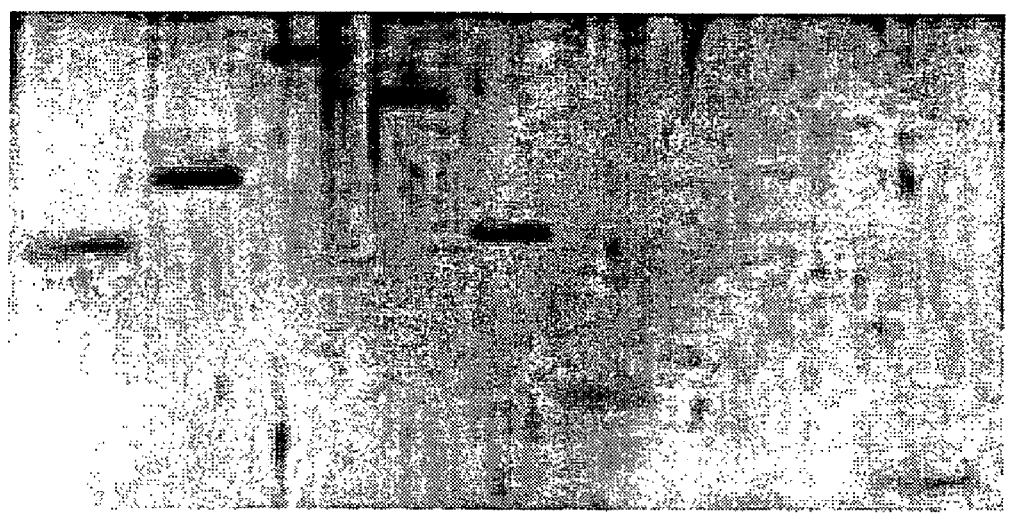

Labeling Experiments with Protein Tyrosine Phosphatases. To investigate the probes' reactivity towards PTPs, a panel of PTP enzymes from all four different PTP-subfamilies was chosen. Thus YopH, hPTP1B, SHP-2 and HePTP for classical intracellular type, DEP-1 for receptor type, VHR and PRL-3 for dual-specific type, and LMW-PTP for low molecular type were chosen for the study. Upon incubating the probes with the panel of PTPs in an appropriate buffer, the protein was separated on SDS-PAGE in denaturing conditions and scanned for fluorescence at optimum excitation wavelength. As shown in FIG. 10, the PTPs were covalently labeled and detected (for simplicity, the labeling of PTPs with Lissamine™ Rhodamine B-PTP probe is shown.). Thus, these fluorescent-based PTP probes can be used to detect active PTPs in complex proteomic mixtures.

Figure 11:
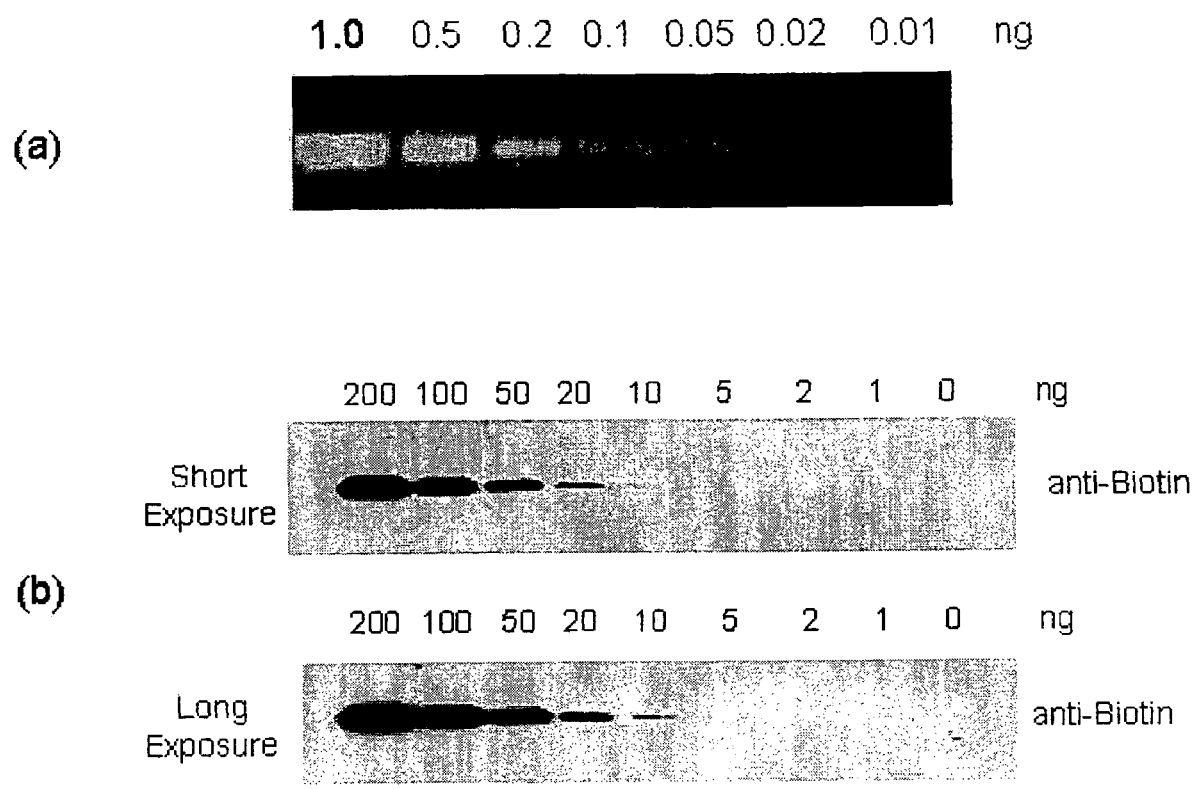
FIG. 11 demonstrates the sensitivity of fluorescence-based PTP probes. (Panel A) Different amount of Lissamine™ rhodamine B Probe-labeled YopH, visualized by direct in-gel fluorescent scanning using Typhoon 9400 scanner. Note that as low as 10 picogram of labeled YopH can be detected. (Panel B) Different amount of Biotin PTP Probe-labeled YopH, detected using anti-biotin antibody. Only 10 nanogram of labeled YopH is detected. This clearly demonstrates that the detection by these fluorescent-based PTP probes is at least 1000-fold more sensitive than antibody based one.

The Fluorescent-Based PTP Probes are Ultra Sensitive. The ability of the fluorescent-based PTP probes to detect labeled PTPs was evaluated and compared directly to an antibody based labeling experiment that used a biotin containing probe. The results in FIG. 11 suggest that detection using fluorescent-based PTP probes is at least 1000-fold more sensitive than that of antibody based methods. For example, using a Lissamine™ rhodamine B-based PTP probe, as little as 10 picogram of labeled YopH, a prototypical PTP, was detected. On the other hand, when employing a biotin-based probe and using antibody based detection the limit of detection was only 10 nanogram of protein. This level of sensitivity of the fluorescent-based probe is quite remarkable.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A compound of Formula A:

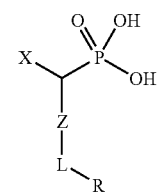

wherein

Z is a para-phenylene group;

X is a halide;

R is a fluorescent protein, a protein having an antigen binding region of an antibody, an enzyme, biotin, a fluorescent moiety, a radioactive moiety, an oligo-His moiety, or digoxigenin; and L is —$CH_2$—NH—, or —$CH_2$—NH—C(O)—$(CH_2)$n-NH— where n=1-10.

2. The compound of claim 1, wherein X is Br.

3. The compound of claim 1, wherein R is biotin.

4. The compound of claim 1, wherein R is a fluorescent moiety.

5. The compound of claim 1, wherein R is an oligo-His moiety.

6. The compound of claim 1, wherein R is a radioactive moiety.

7. The compound of claim 1, comprising an isotopic variant of any atom.

8. The compound of claim 1, wherein L-R is —$CH_2$—NH—R.

9. The compound of claim 1, wherein L-R is —$CH_2$—NH—C(O)—$(CH_2)$n-NH—R, where n=1-10.

10. The compound of claim 9, wherein n=5.

11. The compound of claim 1, wherein the compound is

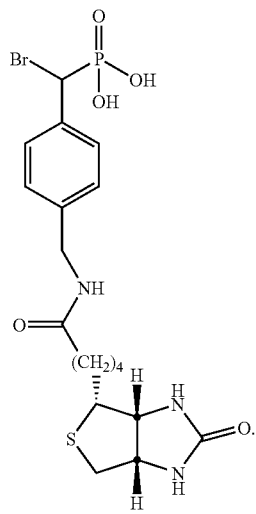

12. A composition comprising the compound of claim 1 covalently bound to a member of the PTP superfamily.

13. The composition of claim 12, wherein the PTP is selected from the group consisting of a PTP1B, a YopH, a SHP1, a SHP2, a MEG2, a PTPX1, a PTPX10, a PEST, a LyPTP, a MEG1, a BDP1, a PTPH1, a PTPD1, a PTPD2, a PTPBAS, a PTPTyp, a CD45, a PTPλ, a LAR, a HePTP, a PTPaD45, a PTPα, a PTPβ, a PTPϵ, a PTPγ, a PTPζ, and a PTPIA2.

14. The compound of claim 1, wherein the compound is

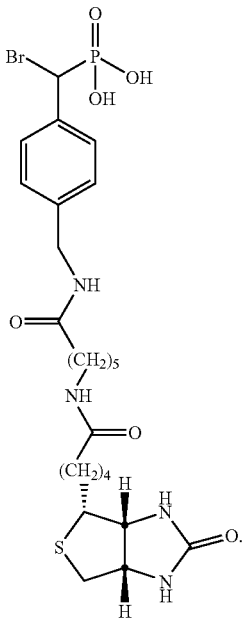

15. The compound of claim 1, wherein the compound is

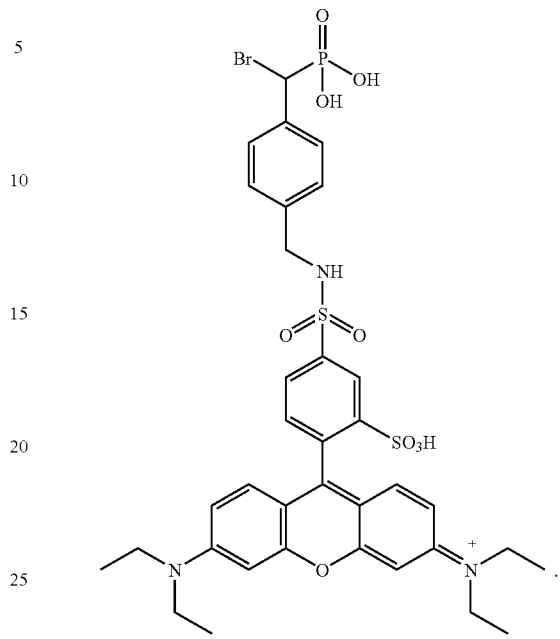

16. The compound of claim 1, wherein the compound is

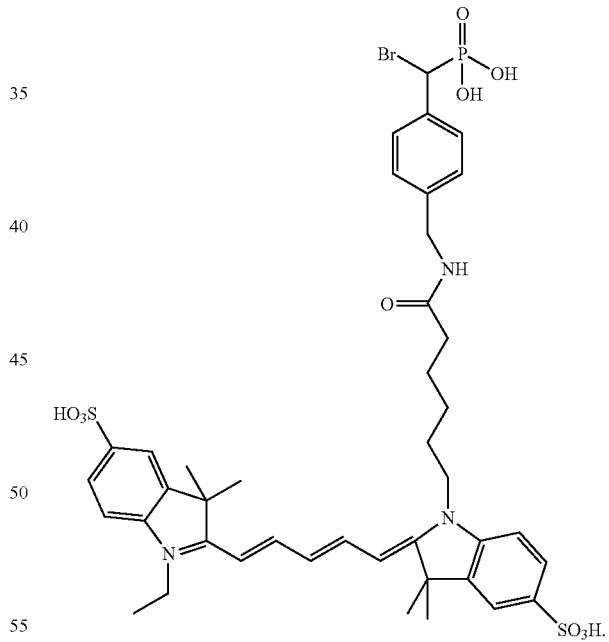

17. The compound of claim 1, wherein R is a protein having an antigen binding region of an antibody, an enzyme or digoxigenin.

* * * * *